United States Patent
Cox

(10) Patent No.: US 10,408,045 B2
(45) Date of Patent: *Sep. 10, 2019

(54) POLYMERIC TRACERS

(71) Applicant: Saudi Arabian Oil Company, Dhahran (SA)

(72) Inventor: Jason R. Cox, Ashland, MA (US)

(73) Assignee: Saudi Arabian Oil Company, Dhahran (SA)

(*) Notice: Subject to any disclaimer, the term of this patent is extended or adjusted under 35 U.S.C. 154(b) by 0 days.

This patent is subject to a terminal disclaimer.

(21) Appl. No.: 16/383,095

(22) Filed: Apr. 12, 2019

(65) Prior Publication Data

US 2019/0242244 A1 Aug. 8, 2019

Related U.S. Application Data

(63) Continuation of application No. 15/800,886, filed on Nov. 1, 2017.
(Continued)

(51) Int. Cl.
*E21B 47/10* (2012.01)
*C09K 8/588* (2006.01)
(Continued)

(52) U.S. Cl.
CPC ........ *E21B 47/1015* (2013.01); *B01D 53/025* (2013.01); *C08F 112/08* (2013.01);
(Continued)

(58) Field of Classification Search
None
See application file for complete search history.

(56) References Cited

U.S. PATENT DOCUMENTS 3,703,355 A * 11/1972 Takahashi et al. .... G01N 31/12
422/78
3,851,171 A * 11/1974 Saniford ............ E21B 47/1015
250/259
(Continued)

FOREIGN PATENT DOCUMENTS

WO 2016/174413 11/2016

OTHER PUBLICATIONS

International Search Report and Written Opinion issued in International Application No. PCT/US2017/059668 dated Dec. 21, 2017; 15 pages.
(Continued)

*Primary Examiner* — Anuradha Ahuja
(74) *Attorney, Agent, or Firm* — Fish & Richardson P.C.

(57) ABSTRACT

Tracing subterranean fluid flow includes providing a first polymeric tracer to a first injector, collecting a first aqueous sample from a first producer, and assessing the presence of the first polymeric tracer in the first aqueous sample. The first polymeric tracer includes a first polymer formed from at least a first monomer. The presence of the first polymeric tracer in the first aqueous sample is assessed by removing water from the first aqueous sample to yield a first dehydrated sample. pyrolyzing the first dehydrated sample to yield a first gaseous sample, and assessing the presence of a pyrolization product of the first polymer in the first gaseous sample. The presence of the pyrolization product of the first polymer in the first gaseous sample is indicative of the presence of a first subterranean flow pathway between the first injector location and the first producer location.

3 Claims, 18 Drawing Sheets

Related U.S. Application Data

(60) Provisional application No. 62/418,433, filed on Nov. 7, 2016.

(51) Int. Cl.
| | |
|---|---|
| *E21B 49/00* | (2006.01) |
| *G01N 30/88* | (2006.01) |
| *G01N 30/84* | (2006.01) |
| *C09K 8/035* | (2006.01) |
| *G01N 30/72* | (2006.01) |
| *C08F 112/08* | (2006.01) |
| *C08F 112/14* | (2006.01) |
| *B01D 53/02* | (2006.01) |

(52) U.S. Cl.
CPC ............ *C08F 112/14* (2013.01); *C09K 8/035* (2013.01); *C09K 8/588* (2013.01); *E21B 49/00* (2013.01); *G01N 30/7206* (2013.01); *G01N 30/84* (2013.01); *G01N 30/88* (2013.01); *C09K 2208/10* (2013.01); *G01N 2030/8405* (2013.01); *G01N 2030/885* (2013.01)

(56) References Cited

U.S. PATENT DOCUMENTS

| | | | | |
|---|---|---|---|---|
| 3,947,396 | A | | 3/1976 | Kangas et al. |
| 4,137,452 | A | * | 1/1979 | Paap .................. E21B 47/1015 250/269.8 |
| 4,264,329 | A | * | 4/1981 | Beckett ............... E21B 47/1015 166/252.6 |
| 4,420,565 | A | * | 12/1983 | Schmitt ............... E21B 47/1015 166/250.12 |
| 4,755,469 | A | * | 7/1988 | Showalter ............... C10L 1/003 436/27 |
| 5,990,224 | A | | 11/1999 | Raynolds et al. |
| 6,331,436 | B1 | * | 12/2001 | Richardson .......... G01N 33/241 436/27 |
| 2001/0036667 | A1 | * | 11/2001 | Tayebi ................. E21B 47/1015 436/56 |
| 2013/0084643 | A1 | * | 4/2013 | Commarieu ............. C09K 8/03 436/27 |
| 2013/0126158 | A1 | * | 5/2013 | Gupta .................... E21B 47/00 166/250.12 |
| 2014/0231077 | A1 | | 8/2014 | Rivero et al. |
| 2014/0260694 | A1 | | 9/2014 | Szlendak |
| 2015/0232748 | A1 | | 8/2015 | Kanj et al. |
| 2016/0061790 | A1 | * | 3/2016 | Zhang ................ G01N 30/7206 73/23.37 |
| 2016/0075937 | A1 | * | 3/2016 | Cannan .................... C09K 8/80 166/250.1 |

OTHER PUBLICATIONS

Asadi et al., "Application of Chemical Tracers in IOR: A Case History," Society of Petroleum Engineers, SPE-126029-MS, Feb. 14-17, 2010, 11 pages.

Christy et al., "Characterization of Natural Organic Matter by Pyrolysis/GC-MS," Environment International, vol. 25, 1999.

Cox et al., "Pyrolyzable Nanoparticle Tracers for Environmental Interrogation and Monitoring," ACS Applied Materials & Interfaces, Apr. 2017, 9(15): 13111-13120.

Greenkorn, "Experimental Study of Waterflood Tracers," Journal Petroleum Technology, SPE-169, 14(1), Jan. 1962, 6 pages.

Serres-Piole et al., "Water tracers in oilfield applications: Guidelines," Journal of Petroleum Science and Engineering, vol. 98-99, Nov. 2012, 18 pages.

Shook et al, "Determining Reservoir Properties and Flood Performance From Tracer Test Analysis," SPE Annual Technology Conference and Exhibition, Oct. 2009, SPE-124614-MS, 19 pages.

Sobeih et al., "Recent trends and developments in pyrolysis-gas chromatography," Journal of Chromatography A, Elsevier, vol. 1186, No. 1-2, Oct. 11, 2007; pp. 51-66.

Wagner, "The Use of Tracers in Diagnosing Interwell Reservoir Heterogeneities—Field Results," SPE-6046, Journal of Petroleum Technology, Nov. 1997, 7 pages.

Wampler, "Applied pyrolysis: an overview," Applied Pyrolysis Handbook, 2007, 26 pages.

\* cited by examiner

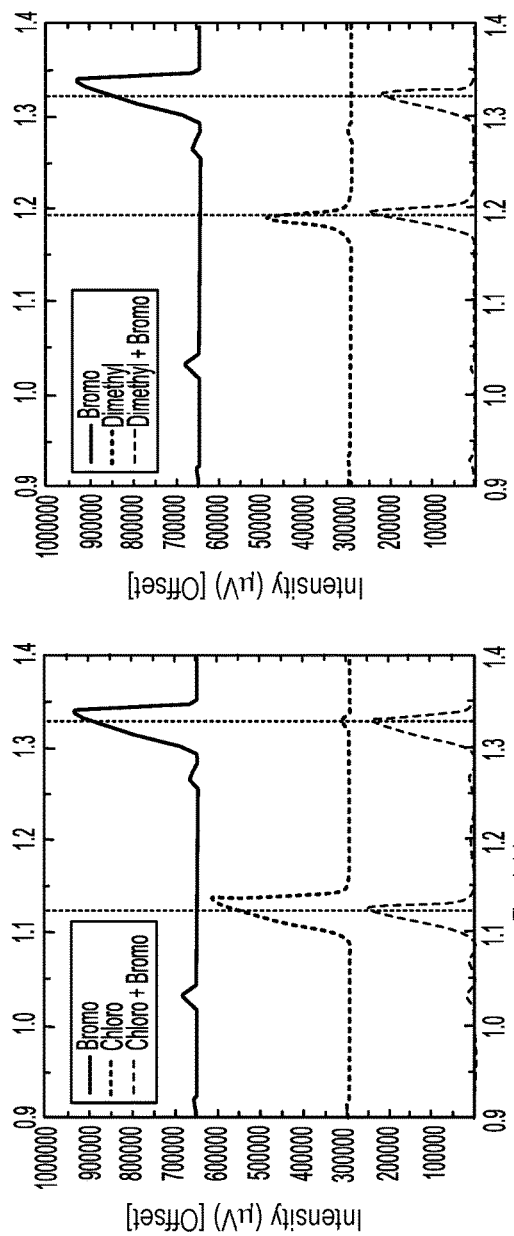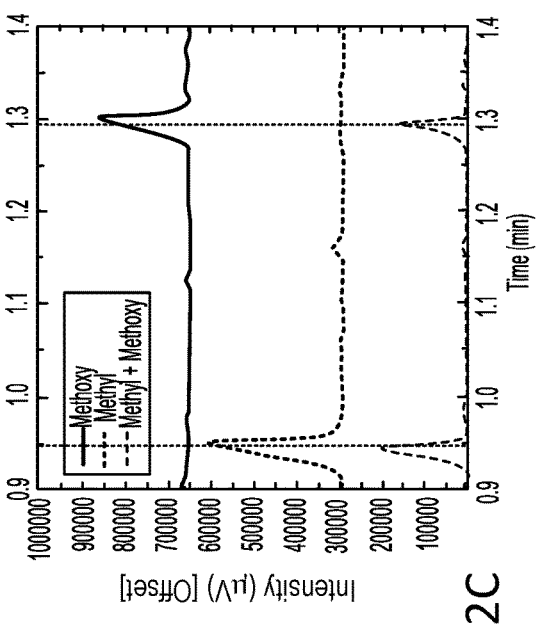
FIG. 12A
FIG. 12B
FIG. 12C

POLYMERIC TRACERS

CROSS-REFERENCE TO RELATED APPLICATION

This application is a continuation of and claims the benefit of priority to U.S. patent application Ser. No. 15/800,886, filed Nov. 1, 2017, which claims the benefit of U.S. Provisional Application Ser. No. 62/418,433 entitled "POLYMERIC TRACERS" and filed on Nov. 7, 2016, both of which are incorporated by reference herein in their entirety.

TECHNICAL FIELD

This document relates to thermal decomposition of polymeric tracers and their detection via pyrolysis gas chromatography-mass spectrometry (GCMS) for oilfield tracer applications.

BACKGROUND

Hydrocarbon bearing reservoirs are complicated, interconnected subterranean systems containing multiple fluid phases. Understanding the connectivity between injection and production wells is a factor in efficient reservoir management as unexpected early water breakthrough at a given well can drastically reduce the oil production rate. Tracer studies provide a means to understand how water is being allocated in the subsurface and to inform the reservoir engineer how to adjust injection rates to mitigate water production. Traditionally, tracer studies are performed by injecting water soluble molecules such as fluorinated benzoic acids and fluorescent dyes such as rhodamine or fluorescein, followed by identification at the producing well via mass spectrometry or fluorescence, respectively. This information may be used to build a map of the fluid pathways in the subsurface environment.

Reservoir simulations of inter-well tracer diffusion over time have demonstrated that tracers injected at different wells may be extracted from a single producer, highlighting the importance of clear and unambiguous tracer signals to aid in distinction. This poses various problems for standard fluorescence-based tracers, which generate overlapping signals given their wide bandwidths of emission (50 nm to 100 nm). This problem, compounded with the limited range of fluorescence detection (300 nm to 1200 nm), the background fluorescence of crude petroleum, and the decline of quantum yield and detectability at higher wavelengths, reduces the amount of distinguishable tracers even for small reservoirs with a moderate number of wells. Moreover, since fluorescence is sensitive to the local environment, salinity, temperature, and the presence of dissolved organic matter make quantitation difficult.

There are other drawbacks to using molecular tracers in the oilfield as well. Due to their small size, molecules tend to diffuse to a greater extent within the matrix as compared to larger entities such as particles, polymers and dendrimers. This leads to lower concentrations at the producing well and greater difficulty in detection. Molecular tracers have to be isolated from the aqueous producing fluid because water is not compatible with gas chromatograph-mass spectrometry (GCMS) instrumentation. This is time consuming and expensive. Each unique molecular tracer has to be vetted for reservoir applications by verifying that the proposed tracer does not stick to the reservoir matrix, is thermally stable and uniquely identifiable. Satisfying all of these specifications drastically reduces the number of potential tracers that could be used. Thus, there is a need to develop an alternative platform to molecular tracers that permits the development of a rich barcoding scheme for elucidating connectivities in complicated, interconnected subterranean systems containing multiple fluid phases.

SUMMARY

The disclosed systems and methods relate to detection of tracer materials in saline, aqueous matrices, the capability to barcode a multiplicity of tracers, and wellhead detection capability. Overall, tracer campaigns serve to inform reservoir managers of subsurface flow patterns. This information, in turn, is used to better allocate the fluids to maximize oil recovery.

Thermal decomposition of polymeric tracers provides a method to generate many tens or hundreds of polymeric barcodes which can be unambiguously identified through the use of pyrolysis-GCMS. The sharp and quasi-discrete signals offered by GCMS detectors make them suitable for convoluted inter-well tracer analysis. As an added benefit, GCMS detection is suitable for tracers that differ in mass, therefore eliminating demand for expensive functionalized molecular taggants used in fluorescence and other tracing systems, reducing material costs, and increasing the number of tags suitable for tracing.

This approach also eliminates reliance post harvesting extraction protocols, as the pyrolyzer can be used to remove any water or interferrents from the system. Electrolytes are mitigated due to their extremely high boiling points which are not accessed during pyrolysis. In addition, the disclosed processes have superior atom economy, in that the entire tracer mass contributes to detectable signals.

In a first general aspect, tracing fluid flow in a subterranean formation includes providing a first polymeric tracer to a first injector location in the subterranean formation, collecting a first aqueous sample from a first producer location in the subterranean formation, and assessing the presence of the first polymeric tracer in the first aqueous sample. The first polymeric tracer includes a first polymer formed from at least a first monomer. The presence of the first polymeric tracer in the first aqueous sample is assessed by removing water from the first aqueous sample to yield a first dehydrated sample, pyrolyzing the first dehydrated sample to yield a first gaseous sample, and assessing the presence of a pyrolization product of the first polymer in the first gaseous sample. The presence of the pyrolization product of the first polymer in the first gaseous sample is indicative of the presence of the first polymeric tracer in the first aqueous sample, and the presence of the first polymeric tracer in the first aqueous sample is indicative of the presence of a first subterranean flow pathway between the first injector location and the first producer location.

Implementations of the first general aspect may include one or more of the following features.

In some cases, the pyrolization product of the first polymer includes the first monomer. In certain cases, the pyrolization product of the first polymer is the first monomer.

In some cases, the pyrolization product of the first polymer includes a substituent on the first monomer. In certain cases, the pyrolization product of the first polymer is a substituent on the first monomer.

Some embodiments include forming a diagrammatic representation of subterranean fluid flow in the subterranean formation. The diagrammatic representation typically includes the first injector location, the first producer location, and an indicator of the first subterranean flow pathway if the pyrolization product of the first polymer is present in the first gaseous sample.

Certain embodiments include providing a second polymeric tracer to a second injector location, collecting a second aqueous sample from the first producer location, and assessing the presence of the second polymeric tracer in the second aqueous sample. The second polymeric tracer includes a second polymer formed from at least a second monomer. The second monomer differs in mass from the first monomer, and the second aqueous sample differs from the first aqueous sample. Assessing the presence of the second polymeric tracer in the second aqueous sample includes removing water from the second aqueous sample to yield a second dehydrated sample, pyrolyzing the second dehydrated sample to yield a second gaseous sample, and assessing the presence of a pyrolization product of the second polymer in the second gaseous sample. The presence of the pyrolization product of the second polymer in the second gaseous sample is indicative of the presence of the second polymeric tracer in the second aqueous sample, and the presence of the second polymeric tracer in the second aqueous sample is indicative of the presence of a second subterranean flow pathway between the second injector location and the first producer location.

In some cases, the pyrolization product of the second polymer includes the second monomer. In certain cases, the pyrolization product of the second polymer is the second monomer.

In some cases, the pyrolization product of the second polymer includes a substituent on the second monomer. In certain cases, the pyrolization product of the second polymer is a substituent on the second monomer.

Some embodiments include forming a diagrammatic representation of subterranean fluid flow in the subterranean formation. The diagrammatic representation typically includes the first injector location, the second injector location, the first producer location, an indicator of the first subterranean flow pathway if the pyrolization product of the first polymer is present in the first gaseous sample, and an indicator of the second subterranean flow pathway if the pyrolization product of the second polymer is present in the second gaseous sample.

Some embodiments include providing a second polymeric tracer to a second injector location and assessing the presence of the second polymeric tracer in the first aqueous sample. The second polymeric tracer includes a second polymer formed from at least a second monomer. The second monomer differs in mass from the first monomer. Assessing the presence of the second polymeric tracer in the first aqueous sample includes assessing the presence of a pyrolization product of the second polymer in the first gaseous sample. The presence of the pyrolization product of the second polymer in the first gaseous sample is indicative of the presence of the second polymeric tracer in the first aqueous sample, and the presence of the second polymeric tracer in the first aqueous sample is indicative of the presence of a second subterranean flow pathway between the second injector location and the first producer location. The presence of the first subterranean flow pathway and the second subterranean flow pathway is indicative of fluid connectivity between the first subterranean flow pathway and the second subterranean pathway.

Certain embodiments include forming a diagrammatic representation of subterranean fluid flow in the subterranean formation. The diagrammatic representation typically includes the first injector location, the second injector location, the first producer location, an indicator of the first subterranean flow pathway if the pyrolization product of the first polymer is present in the first gaseous sample, an indicator of the second subterranean flow pathway if the pyrolization product of the second polymer is present in the first gaseous sample, and an indicator of the fluid connectivity between the first subterranean pathway and the second subterranean pathway if the pyrolization product of the first polymer and the pyrolization product of the second polymer are both present in the first gaseous sample.

In some cases, a length of time between providing the first polymeric tracer and collecting the first aqueous sample is in a range of days to years.

In some cases, the pyrolization product of the first polymer is not present in the first gaseous sample. In these cases, embodiments include collecting a second aqueous sample from the first producer location in the subterranean formation, and assessing the presence of the first polymeric tracer in the second aqueous sample. A length of time between providing the first polymeric tracer and providing the second polymeric tracer may be in a range of days to years.

In one example, the first polymeric tracer includes a first polymeric nanoparticle. The first polymeric nanoparticle may include a polymeric coating over a polymeric core, where the polymeric core comprises the first polymer. In some examples, the first polymer includes polystyrene, polyacrylate, polymethacrylate, or a vinyl polymer.

Some embodiments include removing water from the first aqueous sample. Removing water from the first aqueous sample may include heating the first aqueous sample for a first length of time at a first temperature greater than the boiling point of water, where the degradation temperature of the first polymer is greater than the first temperature. In some examples, the first temperature is in a range of 200° C. to 400° C. In some examples, the first length of time in a range of 10 seconds to 2 minutes, the second length of time is in a range of 10 seconds to 2 minutes, or both.

Some embodiments include pyrolyzing the first dehydrated sample. Pyrolyzing the first dehydrated sample may include heating the first dehydrated sample for a length of time to a temperature greater than the degradation temperature of the first polymer.

In some embodiments, assessing the presence of the pyrolization product of the first polymer in the first gaseous sample includes providing the first gaseous sample to a gas chromatograph to yield an output including components of the first gaseous sample. Assessing the presence of the pyrolization product of the first polymer in the first gaseous sample may include providing the output of the gas chromatograph to a detector. In some examples, the detector includes a mass spectrometer or a flame ionization detector.

In some embodiments, the first aqueous sample includes saline.

Some embodiments include collecting a second aqueous sample from a second producer location in the subterranean formation, and assessing the presence of the first polymeric tracer in the second aqueous sample. Assessing the presence of the first polymeric tracer in the second aqueous sample may include removing water from the second aqueous sample to yield a second dehydrated sample, pyrolyzing the second dehydrated sample to yield a second gaseous sample, and assessing the presence of the pyrolization product of the first polymer in the second gaseous sample. The presence of the pyrolization product of the first polymer in the second gaseous sample is usually indicative of the presence of the first polymeric tracer in the second aqueous sample, and the presence of the first polymeric tracer in the second aqueous sample is usually indicative of the presence of a second subterranean flow pathway between the first injector location and the second producer location.

In a second general aspect, a polymeric tracer includes a polymeric core, a polymeric layer surrounding the polymeric core, and a surfactant layer between the polymeric core and the polymeric layer. The polymeric core includes a polymer that thermally depolymerizes above the degradation temperature of the polymer into one or more pyrolization products.

Implementations of the second general aspect may include one or more of the following features.

The polymeric tracer may be a nanoparticle. In some cases, the polymer is formed from at least one of a polystyrene, a polyacrylate, a polymethacrylate, or a vinyl monomer. In certain cases, the polymer is a copolymer. The one or more pyrolization products may include one or more constituent monomers of the polymer. In one example, at least one of one or more constituent monomers is the reaction product of a vinylaniline and an epoxide. In another example, the surfactant layer includes sodium dodecyl sulfate. In yet another example, the polymeric layer includes polyethyleneimine.

In a third general aspect, a polymeric tracer library includes a multiplicity of polymeric tracers, each polymeric tracer comprising a polymeric core, and each polymeric core comprising a polymer that thermally depolymerizes into one or more pyrolization products. Each pyrolization product of the multiplicity of polymeric tracers differs in molecular mass from the other pyrolization products of the multiplicity of polymeric tracers.

Implementations of the third general aspect may include one or more of the following features.

Each polymeric tracer may be a nanoparticle. In some embodiments, at least one pyrolization product of each polymer includes or is a constituent monomer of that polymer. In certain embodiments, at least one pyrolization product of each polymer includes or is a substituent of a constituent monomer of that polymer.

The details of one or more implementations of the subject matter described in this specification are set forth in the description below. Other features, aspects, and advantages of the subject matter will become apparent from the description and the claims.

BRIEF DESCRIPTION OF THE DRAWINGS

FIGS. 12A-12C show pyrograms of copolymeric nanoparticles cross-referenced to pyrograms of their constituent monomers.

DETAILED DESCRIPTION

Figure 1:
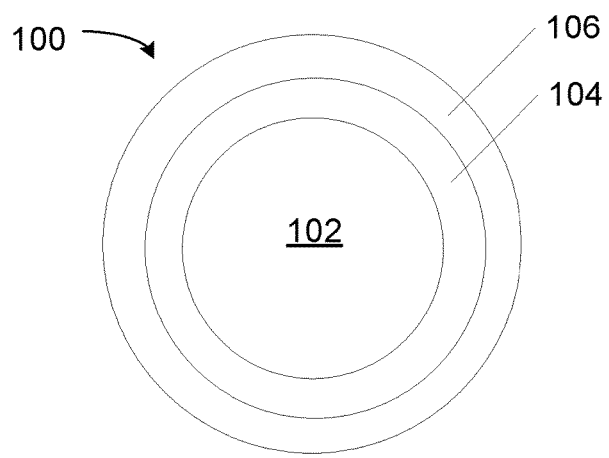
FIG. 1 depicts a polymeric tracer.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (for example, 1%, 2%, 3%, and 4%) and the sub-ranges (for example, 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

In the methods of manufacturing, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" can allow for a degree of variability in a value or range, for example, within 10%, within 5%, or within 1% of a stated value or of a stated limit of a range.

The term "about" refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The phrase "degree of polymerization" is the number of repeating units in a polymer.

The term "polymer" refers to a molecule having at least one repeating unit and can include copolymers.

The term "copolymer" refers to a polymer that includes at least two different repeating units. A copolymer can include any suitable number of repeating units.

The term "fluid" refers to gases, liquids, gels, and critical and supercritical materials.

The phrase "subterranean formation" refers to any material under the surface of the earth, including under the surface of the bottom of the ocean. For example, a subterranean formation can be any section of a wellbore and any section of a subterranean petroleum- or water-producing formation or region in fluid contact with the wellbore. Placing a material in a subterranean formation can include contacting the material with any section of a wellbore or with any subterranean formation in fluid contact with a section of a wellbore. In some examples, a subterranean formation can be any below-ground region that can produce liquid or gaseous petroleum materials, water, or any section below-ground in fluid contact with a below-ground region that can produce liquid or gaseous petroleum materials or water. For example, a subterranean formation can be at least one of an area desired to be fractured, a fracture or an area surrounding a fracture, and a flow pathway or an area surrounding a flow pathway. A fracture or a flow pathway can be optionally fluidly connected to a subterranean petroleum- or water-producing region, directly or through one or more fractures or flow pathways.

A "flow pathway" downhole can include any suitable subterranean flow pathway through which two subterranean locations are in fluid connection. The flow pathway can be sufficient for petroleum or water to flow from one subterranean location to the wellbore or vice-versa. A flow pathway can include at least one of a hydraulic fracture, and a fluid connection across a screen, across gravel pack, across proppant, including across resin-bonded proppant or proppant deposited in a fracture, and across sand. A flow pathway can include a natural subterranean passageway through which fluids can flow. In some embodiments, a flow pathway can be a water source and can include water. In some embodiments, a flow pathway can be a petroleum source and can include petroleum. In some embodiments, a flow pathway can be sufficient to divert from a wellbore, fracture, or flow pathway connected thereto at least one of water, a downhole fluid, or a produced hydrocarbon.

Polymeric Tracers

Polymeric tracers are detectable tracers that are suitable for tracing subterranean fluid flow in a subterranean formation. Polymeric tracers may be used to provide a multiplicity of unique tracers for large scale tracer campaigns, thereby permitting multi-well interrogation simultaneously. For example, if a field contains multiple injectors and producers, each injector may be treated with a unique polymeric tracer in order to know with certainty which injector is communicating with which producer. It is often the case that multiple injectors will be communicating with a single producer, thereby complicating the situation further. The disclosed polymeric tracers permit the development of a rich barcoding scheme for large scale tracer campaigns.

Polymeric tracers include molecular structures that have a multiplicity of monomers held together by covalent bonds and that thermally decompose to yield smaller fragments, such as the monomers, substituents on the monomers, or other fragments that can be detected in the gas phase. Suitable molecular structures include water-soluble polymers (including water-soluble copolymers), water-soluble dendrimers, polymeric nanoparticles, and the like.

The term "nanoparticle" generally refers to a particle having a largest dimension of up to 100 nm. The nanoparticle may be a coated nanoparticle. In some embodiments, the nanoparticles or coated nanoparticles have a particle size or average size of 10 nm to 100 nm. The term "average size" generally refers to the arithmetic mean of the distribution of nanoparticle sizes in a plurality of nanoparticles. In some examples, the nanoparticles or coated nanoparticles can have a particle size or average size of 20 nm to 80 nm, 30 nm to 50 nm, or less than 100 nm. Nanoparticle size can be determined by dynamic light scattering prior to forming a coated nanoparticle or by scanning electron microscopy after formation of a coated nanoparticle. In some embodiments, a coated nanoparticle has a hydrodynamic diameter of 10 nm to 100 nm. For example, a coated nanoparticle can have a hydrodynamic diameter of 20 nm to 80 nm, 30 nm to 50 nm, or less than 100 nm. The degree of polymerization n of a polymer in a polymeric tracer may be in a range of 5 to 1,000,000.

FIG. 1 depicts a cross section of exemplary polymeric tracer 100. In some implementations, polymeric tracer 100 is a polymeric nanoparticle. Polymeric tracer 100 typically includes polymeric core 102 and one or more coating layers surrounding the polymeric core. As depicted in FIG. 1, polymeric tracer 100 is coated with surfactant layer 104 and polymeric layer 106.

Polymeric core 102 includes a polymer formed from at least a first monomer. In some cases, the polymer is formed from a single monomer. In certain cases, the polymer is a copolymer formed from two or more monomers, each monomer having a different mass. A suitable polymer for the polymeric core depolymerizes into its constituent monomer or monomers, substituents on the monomers and the polymer backbone, or other fragments at temperatures greater than its degradation temperature. The "degradation temperature" of a polymer is generally understood to be the temperature at which the rate of polymerization and depolymerization of the polymer are equal. The degradation temperature of a polymer is typically in range from 200° C. to 1000° C.

Polymers may depolymerize by various mechanisms, based at least in part on relative bond strengths present in the polymer. Monomer reversion occurs when bonds created during polymerization are among the weakest bonds in the polymer, and the polymer thermally degrades to yield the monomer(s) from which the polymer is formed. Examples of polymers that depolymerize by monomer reversion include styrenes and methacrylates. In side-chain scission, substituents on the monomer are among the weakest bonds in the polymer, and these bonds are broken when the polymer is heated to yield the substituents and the polymer backbone. An example of a polymer that depolymerizes by side-chain scission is poly(vinyl chloride). In random scission, bond strengths in the polymer differ so little that thermal degradation of the polymer results in a range of products. Examples of polymers that depolymerize by random scission include polyethylene and polypropylene.

Figure 2:
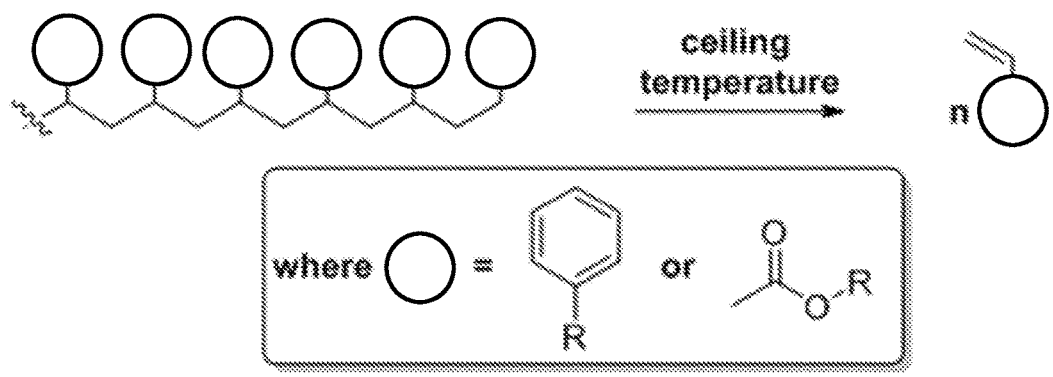
FIG. 2 depicts depolymerization of a polymer at a temperature greater than its degradation temperature.

FIG. 2 depicts an example of monomer reversion of a polymer at a temperature greater than the degradation temperature of the polymer to yield the constituent monomer of the polymer, where R is a substituent. In some examples, R is halogen, alkyl, alkoxy, aminoalkyl, or perfluoroalkyl. Polymers that depolymerize into their constituent monomer or monomers at a temperature greater than the degradation temperature include polystyrenes, polyacrylates, polymethacrylates, and vinyl polymers formed from styrenic, acrylic, methacrylic, and vinyl monomers, respectively. Although FIG. 2 depicts styrenic and acrylic monomers having a single substituent, other suitable monomers are not so limited. Examples of suitable styrenic monomers include methylstyrene (such as 4-methylstyrene, α-methylstyrene), methoxystyrene (such as 4-methoxystyrene), dimethylstyrene (such as 2,4-dimethylstyrene), trimethylstyrene (such as 2, 4, 6-trimethylstyrene), halostyrenes (such as 4-chlorostyrene, 4-flourostyrene and 4-bromostyrene), 4-acetoxystyrene, 4-benzhydrylstyrene, 4-benzyloxy-3-methoxystyrene, 4-tert-butoxystyrene, 2,6-dichlorostyrene, 2,6-difluorostyrene, 3,4-dimethoxystyrene, 2,4-dimethylstyrene, 4-ethoxystyrene, pentafluorophenyl 4-vinylbenzoate, 2,3,4, 5,6-pentafluorostyrene, 4-(trifluoromethyl)styrene, 4-vinylbenzocyclobutene, 4-chloromethylstyrene, 4-vinylbiphenyl, 4-vinylbenzoic acid, 1,1-diphenylethylene, 3,5-bis(trifluoromethyl)styrene, 4-vinylphenyl acetate, trimethoxy(4-vinyl-phenyl)silane, 4-vinylaniline, 4-(aminomethyl)styrene, 4-isopropenylaniline, 1-(4-vinylphenyl)-ethanamine, 1-(4-vinylphenyl)cyclopropanamine, (1S)-1-(3-vinylphenyl)-1, 2-ethanediamine, and 4-vinylphenol.

Examples of suitable epoxides include 1,2-epoxybutane, 1,2-epoxypentane, 1,2-epoxyhexane, 1,2-epoxyoctane, 1,2-epoxydodecane, 1,2-epoxytetradecane, 1,2-epoxyhexadecane, 2-hexadecyloxirane, allyl glycidyl ether, butyl glycidyl ether, tert-butyl glycidyl ether, 3,4-epoxy-1-butene, 1,2-epoxy-5-hexene, 1,2-epoxy-9-decene, 4-chlorophenyl glycidyl ether, 1,2-epoxy-3-phenoxypropane, (2,3-epoxypropyl)benzene, 2-ethylhexyl glycidyl ether, furfuryl glycidyl ether, glycidyl hexadecyl ether, glycidyl isopropyl ether, glycidyl 4-methoxyphenyl ether, glycidyl 2-methylphenyl ether, glycidyl 2,2,3,3,4,4,5,5-octafluoropentyl ether, 2,3-epoxy-1-(1-ethoxyethoxy)propane, 1,2-epoxydecane, 1,2-epoxyoctadecane, 1,2-epoxyeicosane, 2,2,3,3,4,4,5,5,5-nonafluoropentyloxirane, 2,2,3,3,4,4,5,5,6,6,7,7,7-tridecafluoroheptyloxirane, 1,2-epoxy-1H,1H,2H,3H,3H-heptadecafluoroundecane, glycidyl methyl ether, ethyl glycidyl ether, epichlorohydrin, glycidyl propargyl ether, glycidyl lauryl ether, tert-butyldimethylsilyl (S)-glycidyl ether, 3-glycidyloxypropyltrimethoxysilane, 3-glycidyloxypropyl (dimethoxy)methylsilane, [8-(glycidyloxy)-n-octyl] trimethoxysilane, triethoxy(3-glycidyloxypropyl)silane, diethoxy(3-glycidyloxypropyl)methylsilane, 1,1,1,3,5,5,5-heptamethyl-3-(3-glycidyloxypropyl)trisiloxane, 3-[2-(perfluorohexyl)ethoxy]-1,2-epoxypropane, benzyl glycidyl ether, 4-tert-butylphenyl glycidyl ether, 2,4-dibromophenyl glycidyl ether, (S)-glycidyl titryl ether, (S)—N-glycidyl-phthalimide, and 4-glycidyloxycarbazole.

Suitable monomers may also be synthesized by utilizing Reaction 1 (shown below) between vinylaniline and any epoxide to form a styrenic monomer than could in turn be used for nanoparticle synthesis. In addition, variants of vinylaniline that undergo Reaction 1 could also be used.

Reaction 1

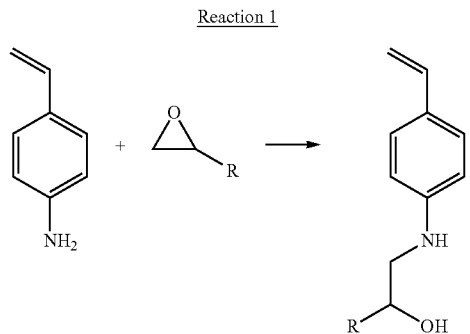

The polymeric core may be formed in a monomer starved addition process. Monomer starved addition is a type of emulsion polymerization. In emulsion polymerization, a surfactant is used to disperse non-water-soluble monomer in an aqueous phase, and an initiator is added to initiate polymerization inside the micelle monomer droplets. In monomer starved addition, monomer is provided at a rate less than the polymerization rate. This allows control of the resulting particle size, since there is no excess monomer and thus no opportunity for any particle to grow faster than another or for any droplets to form.

Polymeric core 102 is coated with surfactant layer 104. Surfactant layer 104 serves to stabilize monomer droplets during polymerization, and to provide an electrostatic charge on the periphery of the nanoparticle, thereby facilitating coating with an additional polymer of opposite charge. Suitable surfactants include anionic surfactants such as alkyl sulfates, fatty alcohol ether sulfates, alkyl phenol ether sulfates, poloxamers, alkyl ammonium halides, and others generally known in the art of emulsion polymerization. In some examples, suitable surfactants include cetyl trimethyl ammonium bromide and sodium dodecyl sulfate.

Surfactant layer 104 is coated with polymeric layer 106. Polymeric layer 106 serves as a protective coating for polymeric tracer 100. Polymeric layer 106 is substantially inert to aqueous and dried downhole fluid phases including a range of organic and inorganic compounds, such that polymeric core 102 is preserved under saline and thermally stressful reservoir conditions. Polymeric layer 106 may include one or more polymers, each polymer including one or more monomers. In one example, polymeric layer 106 includes polyethyleneimine (PEI). Other suitable polymers for polymeric layer 106 include crosslinked carbohydrate-based coatings and coatings formed from a linker, a cross-linker, and a stabilizing group.

A crosslinked carbohydrate-based coating can include a carbohydrate including a monosaccharide, an oligosaccharide, a polysaccharide, and mixtures thereof. In some embodiments, the polysaccharide is selected from the group consisting of an alginate, a chitosan, a curdlan, a dextran, a derivatized dextran, an emulsan, a galactoglucopolysaccharide, a gellan, a glucuronan, an N-acetyl-glucosamine, an N-acetyl-heparosan, a hyaluronic acid, a kefiran, a lentinan, a levan, a mauran, a pullulan, a scleroglucan, a schizophyllan, a stewartan, a succinoglycan, a xanthan, a diutan, a welan, a starch, a derivatized starch, a tamarind, a tragacanth, a guar gum, a derivatized guar gum (for example, a hydroxypropyl guar, a carboxy methyl guar, or a carboxymethyl hydroxypropyl guar), a gum ghatti, a gum arabic, a locust bean gum, a cellulose, and a derivatized cellulose (for example, a carboxymethyl cellulose, a hydroxyethyl cellulose, a carboxymethyl hydroxyethyl cellulose, a hydroxypropyl cellulose, or a methyl hydroxy ethyl cellulose). In some embodiments, the polysaccharide is dextran.

The polysaccharide can have a number average molecular weight of about 1,000 MW to about 150,000 MW. For example, the polysaccharide can have a number average molecular weight of about 10,000 MW to about 140,000 MW, about 30,000 MW to about 130,000 MW, 50,000 MW to about 120,000 MW, 70,000 MW to about 110,000 MW, or about 80,000 MW to about 100,000 MW or about 1,000 MW, 5,000 MW, 10,000 MW, 20,000 MW, 30,000 MW, 40,000 MW, 50,000 MW, 60,000 MW, 70,000 MW, 80,000 MW, 90,000 MW, 100,000 MW, 110,000 MW, 120,000 MW, 130,000 MW, 140,000 MW, or about 150,000 MW or greater.

The polysaccharide can be dextran with a number average molecular weight of about 1,000 MW to about 150,000 MW. For example, the dextran can have a number average molecular weight of about 10,000 MW to about 140,000 MW, about 30,000 MW to about 130,000 MW, 50,000 MW to about 120,000 MW, 70,000 MW to about 110,000 MW, or about 80,000 MW to about 100,000 MW or about 1,000 MW, 5,000 MW, 10,000 MW, 20,000 MW, 30,000 MW, 40,000 MW, 50,000 MW, 60,000 MW, 70,000 MW, 80,000 MW, 90,000 MW, 100,000 MW, 110,000 MW, 120,000 MW, 130,000 MW, 140,000 MW, or about 150,000 MW or greater.

In some embodiments, the crosslinked carbohydrate-based coating is the reaction product of a crosslinking reaction between an epoxide-based compound and a carbohydrate. Crosslinking the carbohydrate-based coating can promote association of the carbohydrate based coating with the underlying nanoparticle. The epoxide-based compound can be selected from the group consisting of polyethylene glycol diglycidyl ether, epichlorohydrin, 1,4-butanediol diglycidyl ether, ethylene glycol diglycidyl ether, 1,6-hexanediol diglycidyl ether, propylene glycol diglycidyl ether, poly(propylene glycol)diglycidyl ether), poly(tetramethylene glycol)diglycidyl ether, neopentyl glycol diglycidyl ether, polyglycerol polyglycidyl ether, diglycerol polyglycidyl ether, glycerol polyglycidyl ether, trimethylpropane polyglycidyl ether, 1,2-(bis(2,3-epoxypropoxy)ethylene), pentaerythritol glycidyl ether, pentaerythritol polyglycidyl ether, sorbitol polyglycidyl ether, and mixtures thereof. In some embodiments, the epoxide-based compound is pentaerythritol glycidyl ether.

The crosslinked carbohydrate-based coating can be the reaction product of a quenching reaction between the crosslinked carbohydrate-based coating and an amine-functionalized compound. Quenching the crosslinked carbohydrate based coating can involve reacting an amine with unreacted epoxides present in the crosslinked, carbohydrate-based coating. Additionally, quenching the unreacted epoxides can serve to prevent undesired crosslinking between nanoparticles. The amine-functionalized compound can have the structure:

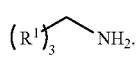

The variable R', at each occurrence, can be independently selected from —H, —OH, or a substituted or unsubstituted ($C_1$-$C_{10}$) hydrocarbyl. For example, the variable $R^1$ can be independently selected from —H, —OH, or —($C_1$-$C_{10}$) alkyl-OH. In some embodiments, the amine-functionalized compound is 2-amino-2-hydroxymethyl-propane-1,3-diol.

In a coating formed from a linker, a crosslinker, and a stabilizing group, the linker may be crosslinked with the crosslinker. The stabilizing group may be covalently bound to the linker. In some embodiments, the linker is crosslinked with the crosslinker and the linker is covalently bound to the stabilizing group.

In some embodiments, the linker includes the subunit:

At each occurrence, the variable $R^1$ can be independently selected from the from the group consisting of —H,

or a linear or branched ($C_1$-$C_{20}$) alkyl interrupted with 0, 1, 2, 3, 4, 5, 6, 7, 8, or 9 substituted or unsubstituted nitrogen atoms, where the wavy line labeled 1 indicates a point of attachment to another linker on the crosslinked-coated nanoparticle. At each occurrence, the variable A can be independently selected from a ($C_1$-$C_{10}$) alkyl interrupted with 0, 1, 2, 3, or 4 oxygen atoms or substituted or unsubstituted nitrogen atoms.

In some embodiments, the linker includes a terminal group, wherein the terminal group is selected from the group consisting of $OR^A_2$, —$SR^A_2$, —N—$NR^A_2$, O—$NR^A_2$, or $NR^A_2$. At each occurrence, the variable $R^A$ is independently selected from —H or

where the wavy line labeled 2 can indicate a point of attachment to the stabilizing group.

In some embodiments, the linker includes polyethylenimine.

The crosslinker can include an epoxide functional group. In some embodiments, the crosslinker is a bis-epoxide. The bis-epoxide can be a diglycidyl ether. The diglycidyl ether can be selected from the group consisting of 1,4-butanediol diglycidyl ether, poly(ethylene glycol) diglycidyl ether, neopentyl glycol diglycidyl ether, glycerol diglycidyl ether, 1,4-cyclohexanedimethanol diglycidyl ether, resorcinol diglycidyl ether, poly(propylene glycol) diglycidyl ether, bisphenol A diglycidyl ether, diglycidyl ether ($C_6H_{10}O_3$), 1,2-propanediol diglycidyl ether, 1,4-butanediyl diglycidyl ether, and combinations thereof. In some embodiments, the diglycidyl ether includes a 1,4-butanediol diglycidyl ether.

The stabilizing group can include one or more of —OH, —$CO_2H$, —$CO_2CH_3$, phosphate, or sulfate. For example, the stabilizing group can include a functional group selected from the group consisting of:

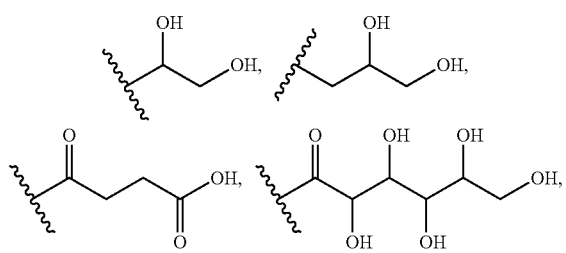

and combinations thereof.

In some implementations, a polymeric tracer library includes a multiplicity of polymeric tracers, each polymeric tracer including one or more polymers suitable for depolymerizing above its degradation temperature into one or more constituent monomers, substituents on the monomers, or other fragments, where each constituent monomer, monomer substituent, or other fragment of the multiplicity of polymeric tracers differs in molecular mass from the other constituent monomers, substituents on the monomers, or other fragments of the multiplicity of polymeric tracers.

Figure 3:
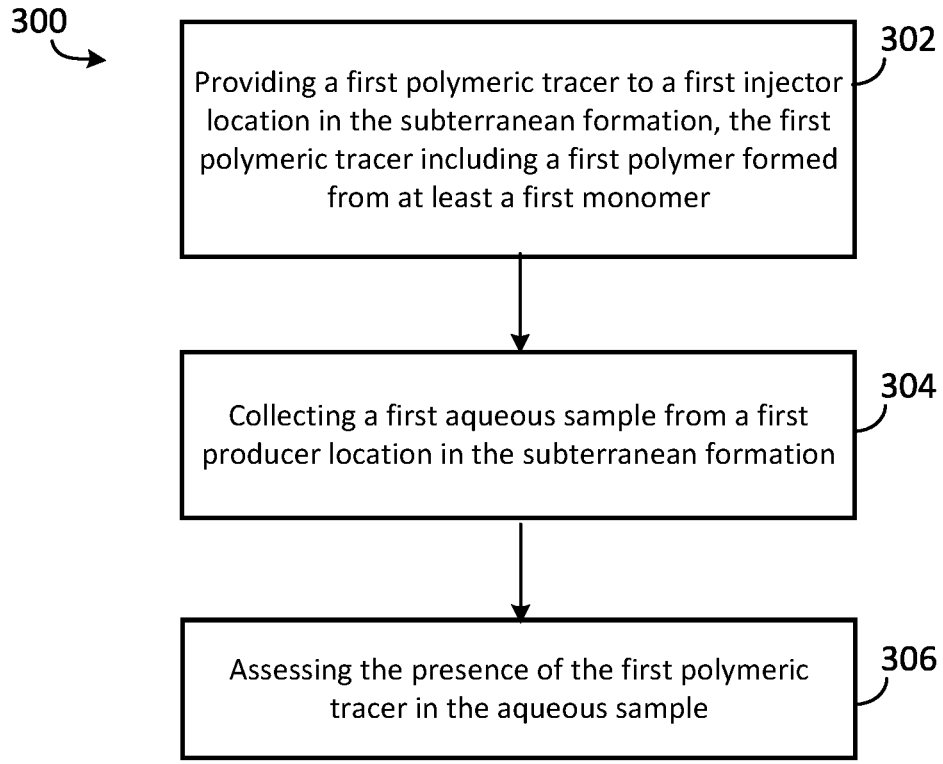
FIG. 3 is a flow chart for a process for tracing subterranean fluid flow from a first injector location to a first producer location in a subterranean formation.

FIG. 3 is a flow chart showing a process 300 for tracing a subterranean fluid flow in a subterranean formation using polymeric tracers. In one example, the subterranean formation is a hydrocarbon bearing reservoir. In 302, a first polymeric tracer is provided to a first injector location in the subterranean formation. The first polymeric tracer includes a first polymer formed from at least a first monomer. In 304, after an elapsed time on the order of days, weeks, months, or years, a first aqueous sample is collected from a first producer location in the subterranean formation. The phrase "aqueous sample" generally refers to a volume of liquid that includes water. The water may include one or more salts, such as sodium chloride. The aqueous sample may include one or more organic compounds that are immiscible with water. In 306, the presence of the first polymeric tracer in the first aqueous sample is assessed.

Figure 4:
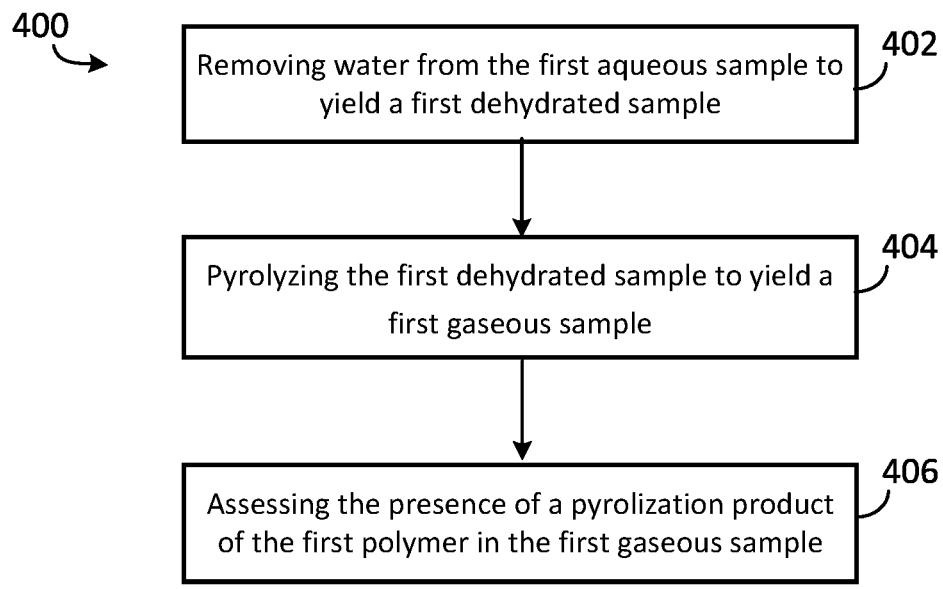
FIG. 4 is a flow chart for a process for assessing the presence of a polymeric tracer in an aqueous sample.

FIG. 4 is a flow chart for a process 400 for assessing the presence of the first polymeric tracer in the first aqueous sample. In 402, water is removed from the first aqueous sample to yield a first dehydrated sample. Removing water from the first aqueous sample includes heating the first aqueous sample to a temperature greater than the boiling point of water and less than the degradation temperature of the first polymer in the first polymeric tracer for a length of time to remove substantially all of the water from the first aqueous sample. In some examples, the first aqueous sample is heated in a range of 200° C. to 500° C., 300° C. to 500° C., or 350° C. to 450° C. for a length of time in a range of 10 sec to 2 min to yield a first dehydrated sample including the first polymeric tracer. When the first aqueous sample includes saline, the first dehydrated sample typically includes salt crystals. The first polymeric tracer may be adsorbed on the salt crystals.

In 404, the first dehydrated sample is pyrolyzed to yield a first gaseous sample. Pyrolyzing the first dehydrated sample includes heating the first aqueous solution to a temperature greater than the degradation temperature of the first polymer and less than the boiling point of sodium chloride for a length of time. Electrolytes are mitigated due to their high boiling points which are not accessed during pyrolysis. In one example, sodium chloride crystals remain unaffected by the pyrolysis, and thus do not interfere with the subsequent analysis of the first gaseous sample. In some cases, the first dehydrated sample is heated to a temperature of at least 100° C., at least 200° C., or at least 300° C. greater than the degradation temperature of the first polymer. In one example, the first dehydrated sample is heated to a temperature in a range of 600° C. to 1000° C., or 700° C. to 900° C. Pyrolyzing the first dehydrated sample depolymerizes the first polymer into pyrolization products including its constituent monomer(s) (that is, the first monomer), substituent(s) on the monomer(s), or other fragments in gaseous form. The gaseous sample also includes degradation products of the surfactant layer and the polymeric layer. This pyrolysis allows for detection of tracer materials in saline, aqueous matrices without extracting the tracer materials from the matrices, as the pyrolyzer can be used to remove any water or interferrents from the first aqueous sample.

The depolymerization process in 404 yields low molecular weight compounds that are amenable to detection by methods such as mass spectrometry (MS) and Fourier transform infrared spectroscopy (FTIR), or by separation via gas chromatography (GC) and subsequent detection by MS or flame ionization detection (FID), Fourier transform infrared spectroscopy (FTIR), and the like. The polymeric core of a polymeric tracer is not compatible with gas chromatography due at least in part to the high molecular weight and low volatility of the polymer. Depolymerization of the polymeric core allows detection of the presence of the polymer in the polymeric core via detection of the monomer constituent of the polymer.

In 406, the presence of a pyrolization product of the first polymer, such as the first monomer, a substituent on the first monomer, or other fragment in the first gaseous sample is assessed. Assessing the presence of the pyrolization product of the first polymer in the first gaseous sample includes providing the first gaseous sample to a gas chromatograph to yield an output including the components of the first gaseous sample, and providing the output of the gas chromatograph to a detector. In one example, the detector is a mass spectrometer. In other examples, the detector is a flame ionization detector, a thermal conductivity detector, or a FTIR detector. The presence of the pyrolization product of the first polymer in the first gaseous sample is indicative of the presence of the first polymeric tracer in the first aqueous sample, and the presence of the first polymeric tracer in the first aqueous sample is indicative of the presence of a first subterranean flow pathway between the first injector location and the first producer location. Thus, if the pyrolization product of the first polymer is present in the first gaseous sample, the first injector location demonstrates fluid connectivity with the first producer location.

By using thermally immolative polymers, the polymeric core can be efficiently decomposed and volatilized into pyrolization products (constituent monomers, substituents on the constituent monomers, or other fragments) upon heating beyond the degradation temperature of the polymer, which can be accomplished using a pyrolysis-detector system in which a pyrolyzer is coupled to a detector. The pyrolyzer allows preheating of an aqueous sample including polymeric tracers to volatize unwanted background components and vent the resulting degradation products to waste before pyrolysis of the polymeric tracers.

The polymeric tracers and associated pyrolization products ("mass tags") demonstrate (i) tag preservation under saline and thermally stressful reservoir conditions, (ii) non-degrading conversion of tags into the gaseous phase for GC compatibility, (iii) adequate tag delivery to the detector after fluid production, and (iv) elimination of background signals from seawater and crude oil.

Figure 5:
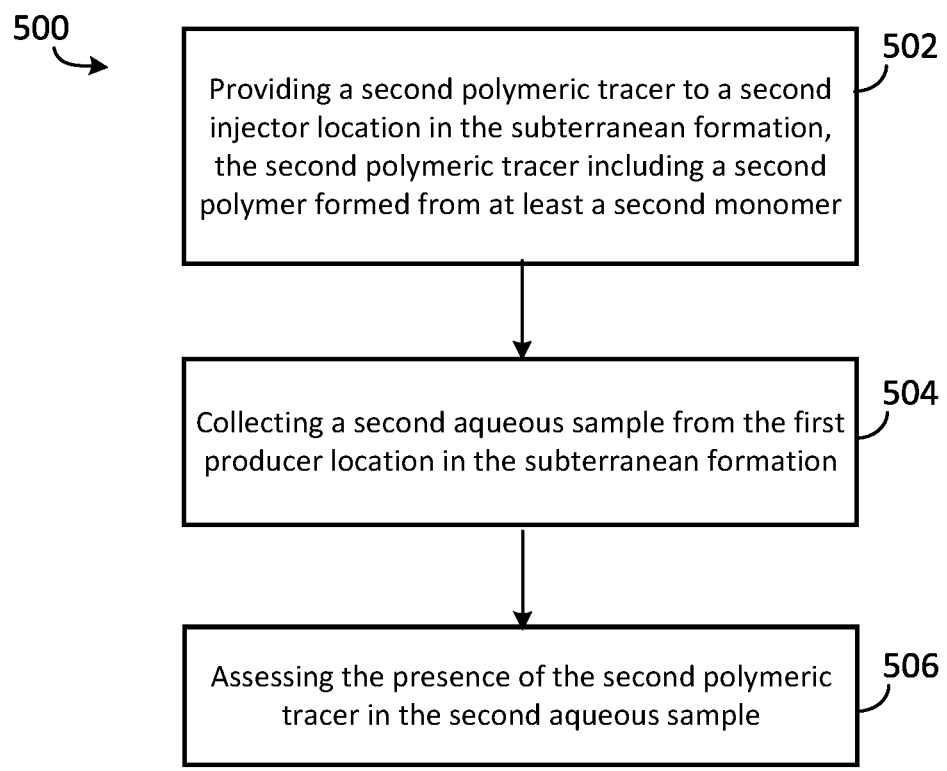
FIG. 5 is a flow chart for a process for tracing subterranean fluid flow from a second injector location to a first producer location in a subterranean formation.

FIG. 5 is a flow chart showing a process 500 for tracing a subterranean fluid flow in the subterranean formation described with respect to FIG. 3, in which a second polymeric tracer is provided to a second injector location, and the presence of the second polymeric tracer in a second aqueous sample from the first producer location is assessed. In 502, a second polymeric tracer is provided to a second injector location in the subterranean formation. The second polymeric tracer includes a second polymer formed from at least a second monomer that differs in mass from the first monomer. In 504, a second aqueous sample is collected from the first producer location in the subterranean formation. The second aqueous sample may be different than the first aqueous sample. In 506, the presence of the second polymeric tracer in the second aqueous sample is assessed. Assessing the presence of the second polymeric tracer in the second aqueous sample may be achieved as described with respect to FIG. 4 for assessing the presence of the first polymeric tracer in the first aqueous sample.

Figure 6:
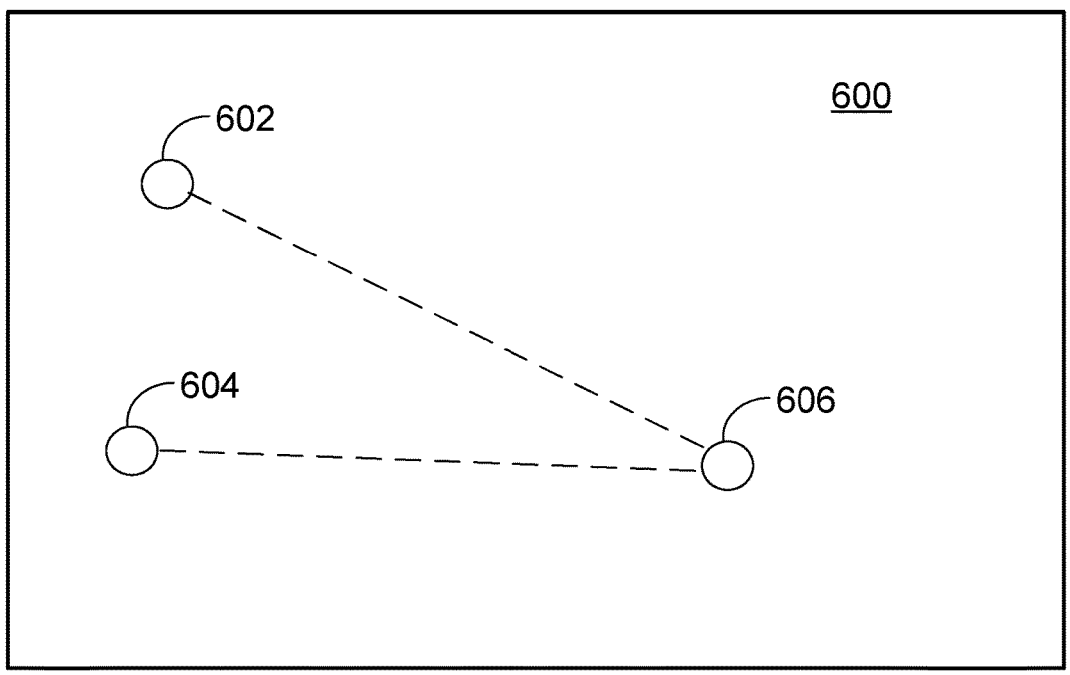
FIG. 6 depicts a diagrammatic representation of subterranean fluid flow from a first injector location and a second injector location to a first producer location in a subterranean formation.

FIG. 6 depicts a diagrammatic representation of subterranean fluid flow in subterranean formation 600 having first injector location 602, second injector location 604, and first producer location 606. A subterranean flow pathway between first injector location 602 and first producer location 606 is depicted by the dashed line between the first injector location and the first producer location. If the pyrolization product of the first polymer is present in the first gaseous sample (that is, if the first polymeric tracer is present in the first aqueous sample), then a subterranean flow pathway exists between first injector location 602 and first producer location 606. If the pyrolization product of the first polymer is not present in the first gaseous sample (that is, if the first polymeric tracer is not present in the first aqueous sample), then a subterranean flow pathway has not been demonstrated between first injector location 602 and first producer location 606. If the pyrolization product of the second polymer is present in the second gaseous sample (that is, if the second polymeric tracer is present in the second aqueous sample), then a subterranean flow pathway exists between second injector location 604 and first producer location 606. If the pyrolization product of the second polymer is not present in the second gaseous sample (that is, if the second polymeric tracer is not present in the second aqueous sample), then a subterranean flow pathway has not been demonstrated between second injector location 604 and first producer location 606.

Figure 7:
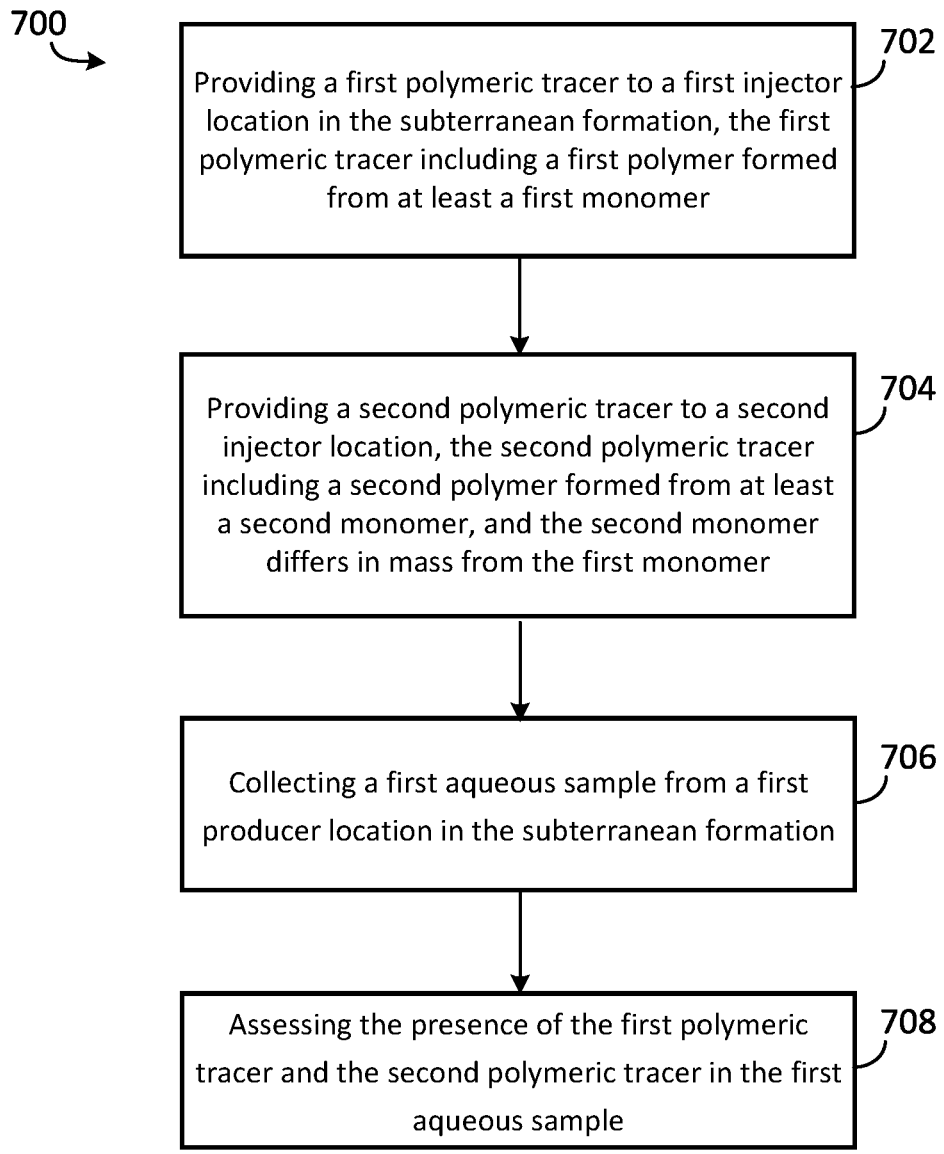
FIG. 7 is a flow chart for a process for tracing subterranean fluid flow from a first injector location and a second injector location to a first producer location in a subterranean formation.

FIG. 7 is a flow chart for a process 700 for tracing subterranean fluid flow in a subterranean formation using polymeric tracers. In 702, a first polymeric tracer is provided to a first injector location in the subterranean formation. The first polymeric tracer includes a first polymer formed from at least a first monomer. In 704, a second polymeric tracer is provided to a second injector location. The second polymeric tracer includes a second polymer formed from at least a second monomer, and the second monomer differs in mass from the first monomer. In 706, a first aqueous sample is collected from a first producer location. In 708, the presence of the first polymeric tracer and the second polymeric tracer in the first aqueous sample is assessed.

Figure 8:
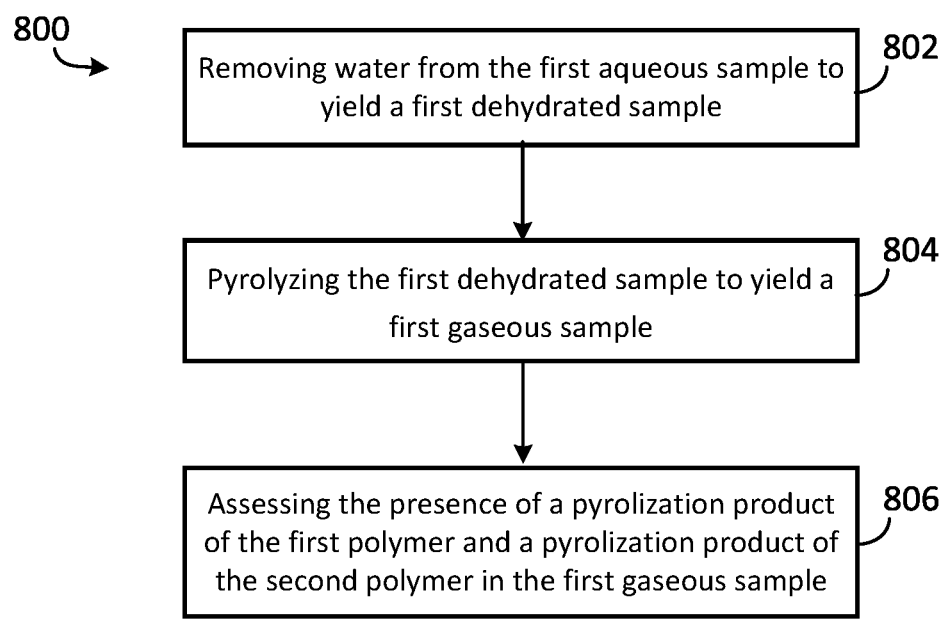
FIG. 8 is a flow chart for a process for assessing the presence of a first polymeric tracer and a second polymeric tracer in an aqueous sample.

FIG. 8 is a flow chart for a process 800 for assessing the presence of the first polymeric tracer and the second polymeric tracer of FIG. 7 in the aqueous sample. Aspects of process 800 may be understood with respect to process 400 as discussed with respect to FIG. 4. In 802, water is removed from the first aqueous sample to yield a first dehydrated sample. Removing water from the first aqueous sample includes heating the first aqueous sample to a temperature greater than the boiling point of water and less than the degradation temperature of the first polymer in the first polymeric tracer and the second polymer in the second polymeric tracer for a length of time to remove substantially all of the water from the first aqueous sample.

In 804, the first dehydrated sample is pyrolyzed to yield a first gaseous sample. Pyrolyzing the first dehydrated sample includes heating the first dehydrated sample to a temperature greater than the degradation temperature of the first polymer and the second polymer for a length of time. Pyrolyzing the first dehydrated sample depolymerizes the first polymer and the second polymer into their pyrolization products (for example, the first monomer and the second monomer or substituents of the first or second monomers or other fragments) in gaseous form.

In 806, the presence of the pyrolization products of the first and second polymers in the first gaseous sample is assessed. Assessing the presence of the pyrolization products of the first and second polymers in the first gaseous sample may include providing the first gaseous sample to a gas chromatograph to yield an output including the components of the first gaseous sample, and providing the output of the gas chromatograph to a detector. In one example, the detector is a mass spectrometer. In another example, the detector is a flame ionization detector. The presence of the pyrolization product of the first polymer in the first gaseous sample is indicative of the presence of the first polymeric tracer in the first aqueous sample, and the presence of the pyrolization product of the second polymer in the first gaseous sample is indicative of the presence of the second polymeric tracer in the first aqueous sample. The presence of the first polymeric tracer in the first aqueous sample is indicative of the presence of a first subterranean flow pathway between the first injector location and the first producer location. The presence of the second polymeric tracer in the first aqueous sample is indicative of the presence of a second subterranean flow pathway between the second injector location and the first producer location. Thus, if the pyrolization product of the second polymer is present in the first gaseous sample, the second injector location has fluid connectivity with the first producer location. The presence of the pyrolization products of the first and second polymers in the first gaseous sample is indicative of a first subterranean flow pathway between the first injector location and the first producer location and a second subterranean flow pathway between the second injector location and the first producer location, as well as fluid connectivity between the first subterranean flow pathway and the second subterranean flow pathway.

Figure 9:
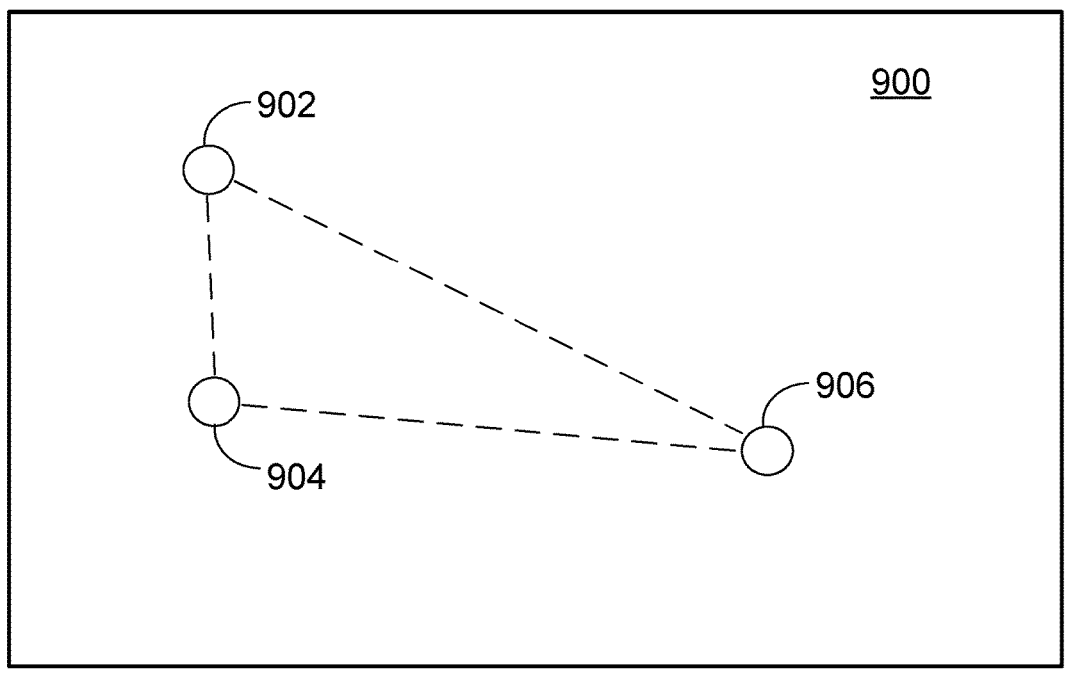
FIG. 9 depicts a diagrammatic representation of subterranean fluid flow from a first injector location and a second injector location to a first producer location in a subterranean formation.

FIG. 9 depicts a diagrammatic representation of subterranean fluid flow in subterranean formation 900 having first injector location 902, second injector location 904, and first producer location 906. A subterranean flow pathway between first injector location 902 and first producer location 906 is depicted by the dashed line between first injector location and the first producer location. If the first monomer is present in the first gaseous sample (that is, if the first polymeric tracer is present in the first aqueous sample), then a subterranean flow pathway exists between first injector location 902 and first producer location 906. If the pyrolization product of the first polymer is not present in the first gaseous sample (that is, if the first polymeric tracer is not present in the first aqueous sample), then a subterranean flow pathway has not been demonstrated between first injector location 902 and first producer location 906. If the pyrolization product of the second polymer is present in the gaseous sample (that is, if the second polymeric tracer is present in the aqueous sample), then there is a subterranean flow pathway between second injector location 904 and first producer location 906. If the pyrolization product of the second polymer is not present in the gaseous sample (that is, if the second polymeric tracer is not present in the aqueous sample), then a subterranean flow pathway has not been demonstrated between second injector location 904 and first producer location 906. Fluid connectivity between first injector location 902 and second injector location 904 is indicated by the dashed line between the first injector location and the second injector location.

In some implementations of process 300 or process 700, a second aqueous sample is collected from a second producer location in the subterranean formation, and the presence of the first polymeric tracer in the second aqueous sample is assessed. Assessing the presence of the first polymeric tracer in the second aqueous sample may be understood with respect to process 400 of FIG. 4, and includes removing water from the second aqueous sample to yield a second dehydrated sample, pyrolyzing the second dehydrated sample to yield a second gaseous sample, and assessing the presence of the pyrolization product of the first polymer in the second gaseous sample. The presence of the pyrolization product of the first polymer in the second gaseous sample is indicative of the presence of the first polymeric tracer in the second aqueous sample, and the presence of the first polymeric tracer in the second aqueous sample is indicative of the presence of a second subterranean flow pathway between the first injector location and the second producer location.

Figure 10:
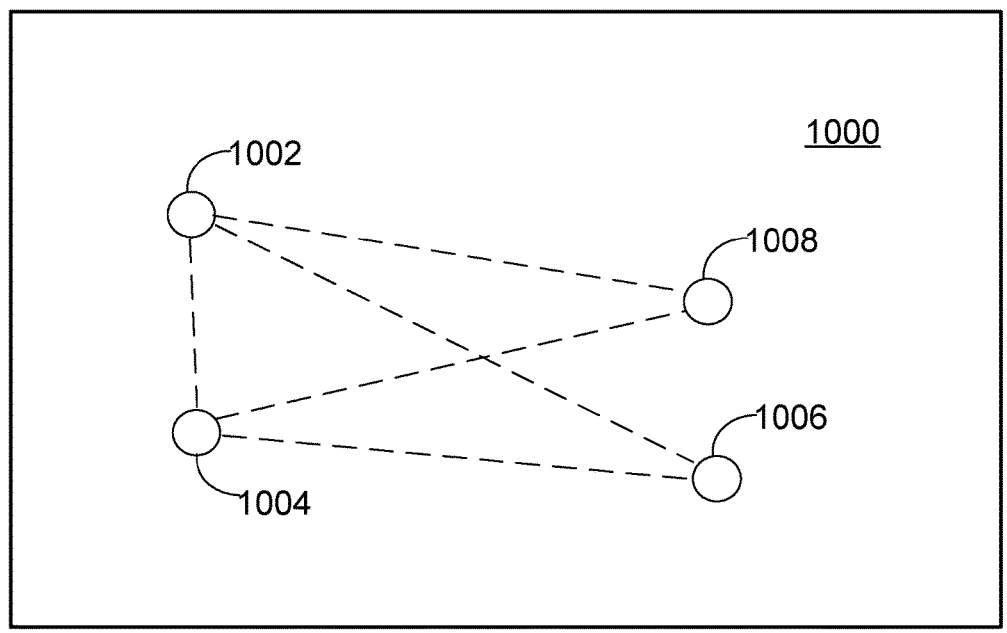
FIG. 10 depicts a diagrammatic representation of subterranean fluid flow from a first injector location and a second injector location to a first producer location and a second producer location in a subterranean formation.

FIG. 10 depicts a diagrammatic representation of subterranean fluid flow in subterranean formation 1000 having first injector location 1002, second injector location 1004, first producer location 1006, and second producer location 1008. A subterranean flow pathway between first injector location 1002 and first producer location 1006 is depicted by the dashed line between the first injector location and the first producer location. If a pyrolization product of the first polymer is present in the gaseous sample (that is, if the first polymeric tracer is present in the aqueous sample), then a subterranean flow pathway exists between first injector location 1002 and first producer location 1006. If a pyrolization product of the first polymer is not present in the first gaseous sample (that is, if the first polymeric tracer is not present in the aqueous sample), then a subterranean flow pathway has not been demonstrated between first injector location 1002 and first producer location 1006. If a pyrolization product of the second polymer is present in the gaseous sample (that is, if the second polymeric tracer is present in the aqueous sample), then a subterranean flow pathway exists between second injector location 1004 and first producer location 1006. If a pyrolization product of the second polymer is not present in the gaseous sample (that is, if the second polymeric tracer is not present in the aqueous sample), then a subterranean flow pathway has not been demonstrated between second injector location 1004 and first producer location 1006. If a pyrolization product of the first polymer is present in the second gaseous sample (that is, if the first polymeric tracer is present in the second aqueous sample), then a subterranean flow pathway exists between first injector location 1004 and second producer location 1008. If a pyrolization product of the first polymer is not present in the second gaseous sample (that is, if the first polymeric tracer is not present in the second aqueous sample), then a subterranean flow pathway has not been demonstrated between first injector location 1002 and second producer location 1008. In some cases, there is fluid connectivity between first injector location 1002 and second injector location 1004 with respect to first producer location 1006, second producer location 1008, or both.

In some implementations, the presence of a polymeric tracer in aqueous samples from a producer location may be assessed over time to establish flow characteristics of the subterranean formation based, for example, on elapsed time between providing the polymeric tracer to the injector location and collecting an aqueous sample including the polymeric tracer from a producer location. Thus, while a particular polymeric tracer may not be present in a first aqueous sample from a first producer location, that polymeric tracer may be present in a second aqueous sample from the first producer location collected after the first aqueous sample.

In some implementations, a multiplicity of polymeric tracers may be used, each including a monomer, substituent on a monomer, or fragment having a mass distinct from that of the others and provided to one of a multiplicity of injector locations, thereby creating a library or barcoding scheme elucidating connectivities in complicated, interconnected subterranean systems. The polymeric core of a polymeric tracer may include a copolymer having two or more constituent monomers, substituents on the monomers, or fragments, each having a different mass. The commercial availability of styrenic, acrylic, methacrylic, and vinyl monomers affords opportunities in barcoding as each monomer has a unique molecular mass and thus a unique fingerprint for various detection methods. The approach also takes advantage of atom economy, in that every atom in the nanoparticle is contributing to signal, thereby increasing the detectability of the polymeric tracers. Moreover, with the disclosed process, the presence of polymeric tracers can be detected without any interference from water or salt. This approach can also be used to detect other materials in the reservoir, including polymers for waterflooding, surfactants for enhanced oil recovery, drilling chemicals, scale inhibitors, corrosion inhibitors, polymeric waste intrinsic to the field water, heavy fractions of crude oil, and the like.

In some implementations, processes 400 and 800 can be automated by using one or more computer-executable programs that are executed using one or more computing devices. In one example, processes 400 and 800 can be executed using one or more computing devices to control removing water from an aqueous sample, pyrolyzing a dehydrated sample, or both, including selecting temperatures and duration for drying the aqueous sample and pyrolyzing the dehydrated sample.

EXAMPLES

Example 1

Polymeric nanoparticles having a styrenic core coated in a layer of surfactant (sodium dodecyl sulfate—SDS) were prepared The nanoparticles were formed using monomer starved addition synthesis in an airtight flask held at 90° C. in an oil bath. 60 mL of SDS (2.55% in deionized water) was added to the flask and left to degas with $N_2$ for 15 minutes. Next, 100 mg of radical initiator [2,2'-azobis(2-methylpropionamidine) dihydrochloride] was added to the flask and left to dissolve. After dissolution of the initiator, a syringe containing the styrenic monomer was connected through a tube to the flask, and 1 mL of monomer solution was injected at 0.02 mL/min using a programmable syringe pump.

The pyrolyzer used was an AS 5250 Pyrolysis Autosampler from CDS Analytical. It was chosen for the dual purpose of pre-heating and selective thermal volatilization to reach each nanoparticle's degradation temperature. Samples were housed in a thin closed-end tube filled with quartz wool. Liquid samples (usually 1 μL) were injected into the wool and held by capillary forces, whereas solids were held between two beds of wool. Tubes were manually loaded into the pyrolyzer's autosampler, which dropped samples into its heating compartment, which was then purged with inert gas (helium). The pyrolyzer then operated in two successive heating stages: drying and pyrolysis. After purging, the exhaust valve shifted to a transfer line to waste, and the sample was dried at a temperature and duration set by the operator, allowing for the removal of unwanted materials that volatilize at temperatures below the pyrolysis temperature. After drying, the valve shifted to a transfer line (held at 300° C.) to the GC column, and the sample was heated to the desired pyrolysis temperature. The pyrolyzer was configured to run programmed temperature stages on a single tube, allowing one to separate the signals of chemicals volatilizing different temperatures.

The GCMS device used was the G908 (beta version) from 908 Devices. Volatilized material from the pyrolyzer was separated by retention time in the GC column. The GC method places the column on a temperature ramp from 40° C. to 300° C. at 1° C./min, and then holds it at 300° C. for 90 sec for a total run time of 6 minutes. The output flow of material from the column is then split between two detectors: the MS and the FID.

Six monomers were purchased for nanoparticle synthesis based on their chemical structures and octanol-water partition coefficients (quantified by predicted log P values). After synthesis, the average particle sizes and concentrations were determined using dynamic light scattering (DLS) and thermogravimetric analysis (TGA), respectively. In addition to the six nanoparticles above, three other nanoparticles with copolymeric cores were also synthesized and characterized. Table 1 lists the six selected monomers with selected characterization parameters.

TABLE 1

Selected monomers with characterization of synthesized nanoparticles.

| Monomer(s) in core | Molecular Weight | log P | Concentration (TGA) | Average Particle Diameter (DLS) |
|---|---|---|---|---|
| p-methylstyrene | 118.18 | 3.16 | 7034 ppm | 8.57 nm |
| p-methoxystyrene | 134.18 | 2.64 | 8570 ppm | 44.29 nm |
| 2,4-dimethylstyrene | 132.20 | 3.62 | 7940 ppm | 13.62 nm |
| 2,4,6-trimethylstyrene | 146.23 | 4.08 | 7050 ppm | 12.90 nm |
| 4-chlorostyrene | 138.59 | 3.22 | 7880 ppm | 14.47 nm |
| 4-bromostyrene | 183.05 | 3.59 | 7660 ppm | 12.12 nm |
| p-methyl + p-methoxy | — | — | 9830 ppm | 91.76 nm |
| 2,4-dimethyl + 4-bromo | — | — | 6490 ppm | 11.63 nm |
| 4-chloro + 4-bromo | — | — | 7180 ppm | 12.61 nm |

The results, summarized in Table 1, show that the synthesis reaction had appreciable yields for each of the monomers given that all concentrations were greater than 6000 ppm. The average particle diameter for most solutions was found to be less than 50 nm, which is suitable for porous transport within a reservoir. Despite similar syntheses, the average diameter of particles containing p-methoxystyrene is notably larger than those of other particles. This is thought to be caused by the monomer's stronger partitioning into water as indicated by its relatively lower log P value.

Figure 11:
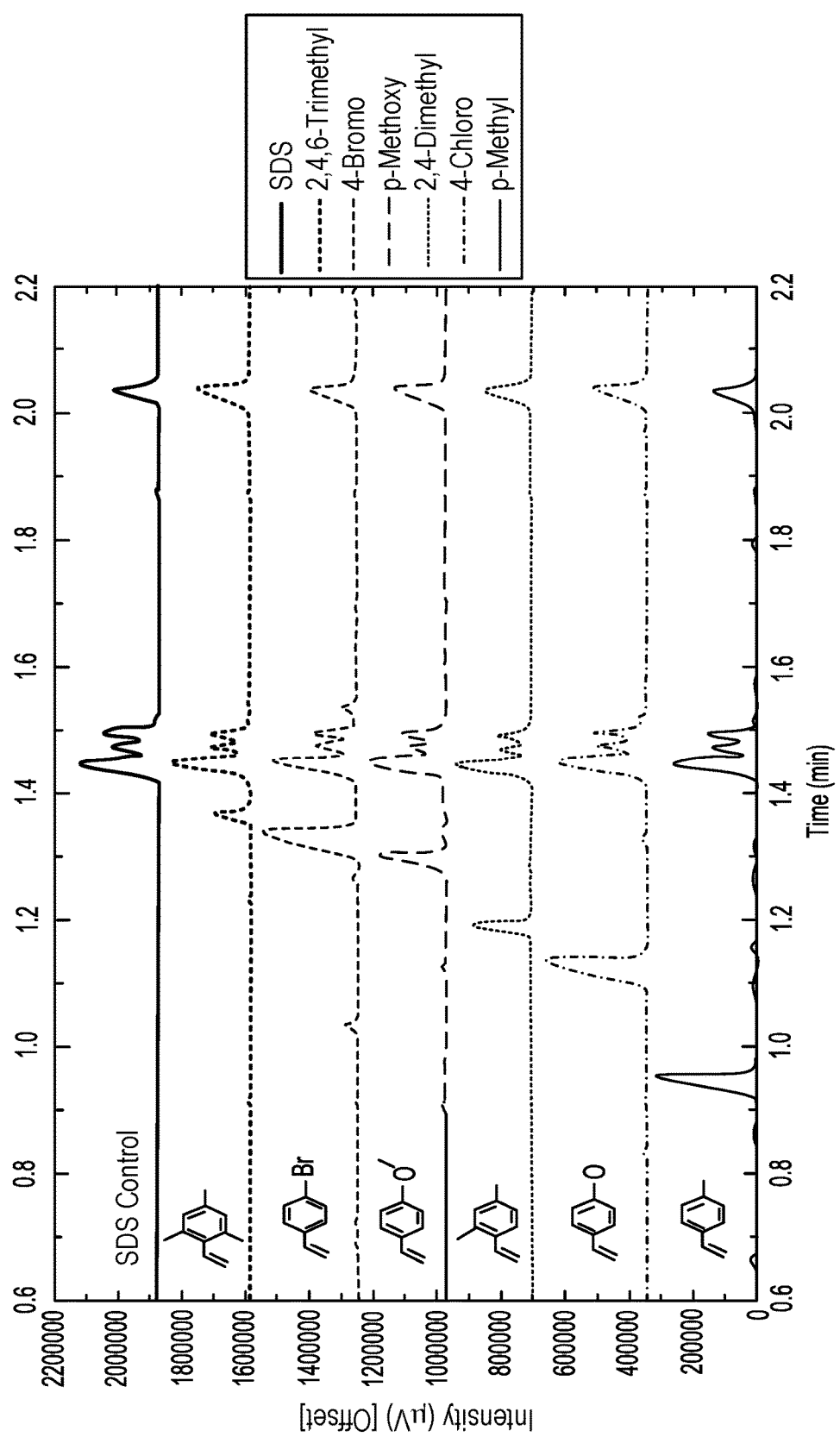
FIG. 11 shows retention times of monomers resulting from pyrolysis of polymeric tracers.

A sample of SDS was first analyzed with pyrolysis-GCFID (Py-GCFID) in order to determine the expected background in each of the nanoparticle solutions. Then each of the nanoparticle solutions was analyzed using the same pyrolysis method, in which samples were dried at 300° C. for 20 sec and pyrolyzed at 800° C. for 15 sec. FIG. 11 shows FID results from pyrolyzing each nanoparticle solution showing distinct signals of varying retention times. Results are compared to the background signal of SDS fragments identified by a triplet peak at 1.45 min and a solitary peak near 2 min.

The background signal of SDS fragments, which is present in all nanoparticle pyrograms given their SDS coating, is characterized by a triplet peak near 1.45 min and a single peak near 2 min. All monomers yielded distinct and reproducible time-separated signals, allowing for each to be identified based on retention time. Table 2 shows a list of retention times for each of the six monomers.

TABLE 2

Monomer retention times.

| Monomer | Retention time (min) |
|---|---|
| p-methylstyrene | 0.95 |
| 4-chlorostyrene | 1.1 |
| 2,4-dimethylstyrene | 1.2 |
| p-methoxystyrene | 1.3 |
| 4-bromostyrene | 1.33 |
| 2,4,6-trimethylstyrene | 1.36 |

The copolymeric nanoparticle solutions were analyzed using the same pyrolysis method, and their pyrograms were compared to those of their constituent monomers. Ignoring the SDS background, each of the copolymeric particles produced two-peak signals at retention times similar to each of its constituent monomers. FIGS. 12A-12C show pyrograms of copolymeric nanoparticles, cross-referenced to pyrograms of their constituent monomers, as the bottom curve of each graph. FIGS. 12A-12C show pyrograms for chloro/bromo, dimethyl/bromo, and methyl/methoxy, respectively. The ability to detect details of composition allows for the use of copolymeric nanoparticles as new distinct tags—significantly increasing the amount of distinguishable tags from a given set of monomers.

To further test the ability of Py-GC to detect details of sample composition, five volumetric mixtures of the 4-chlorostyrene and 4-bromostyrene nanoparticle solutions were prepared—each with a different Cl/Br ratio. The solutions were pyrolyzed using the previously described method, and the intensities of the 4-chlorostyrene and 4-bromostyrene peaks were monitored.

Figure 13:
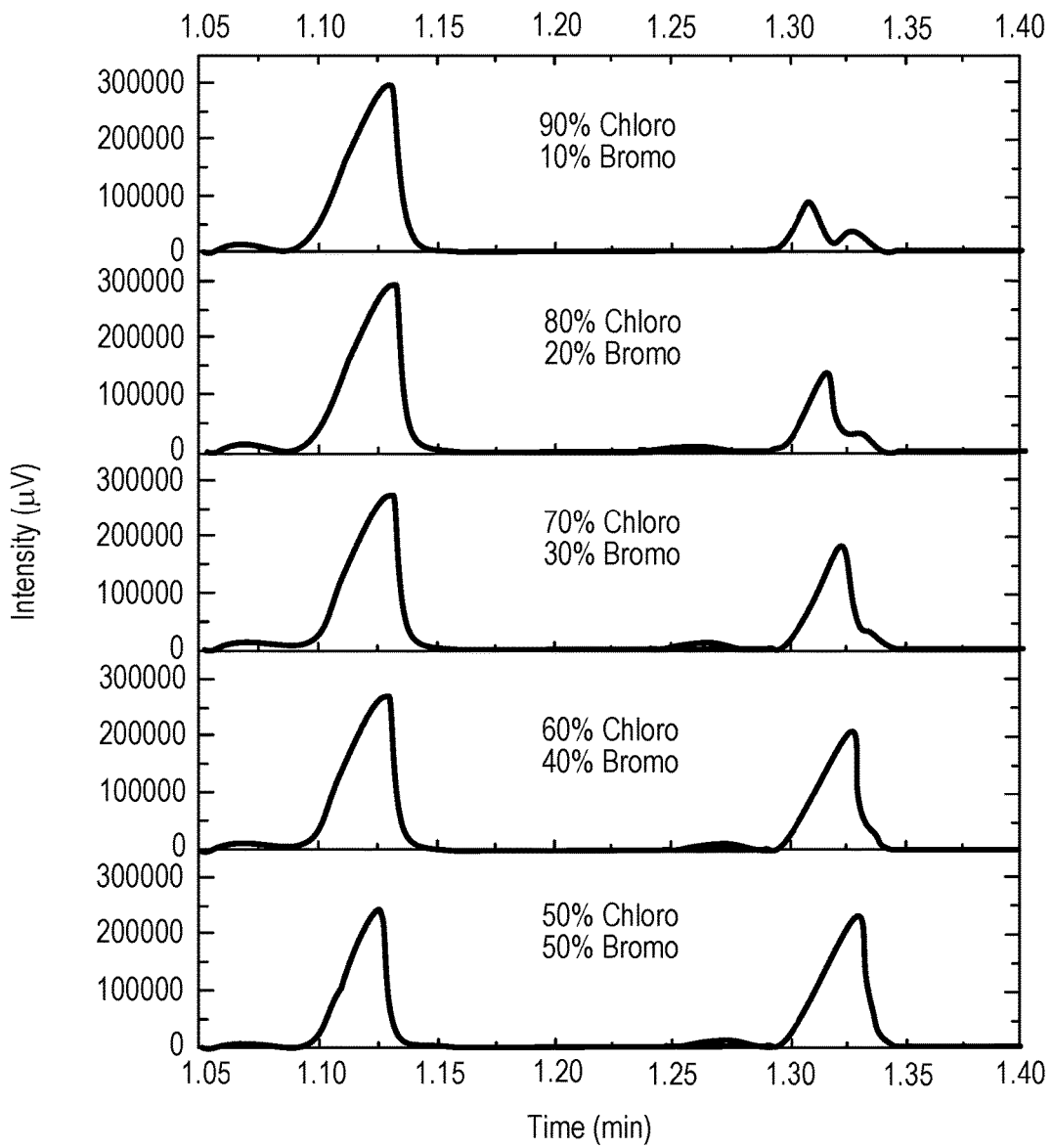
FIGS. 13 and 14 show peak intensity analysis of monomer mixtures.
Figure 14:
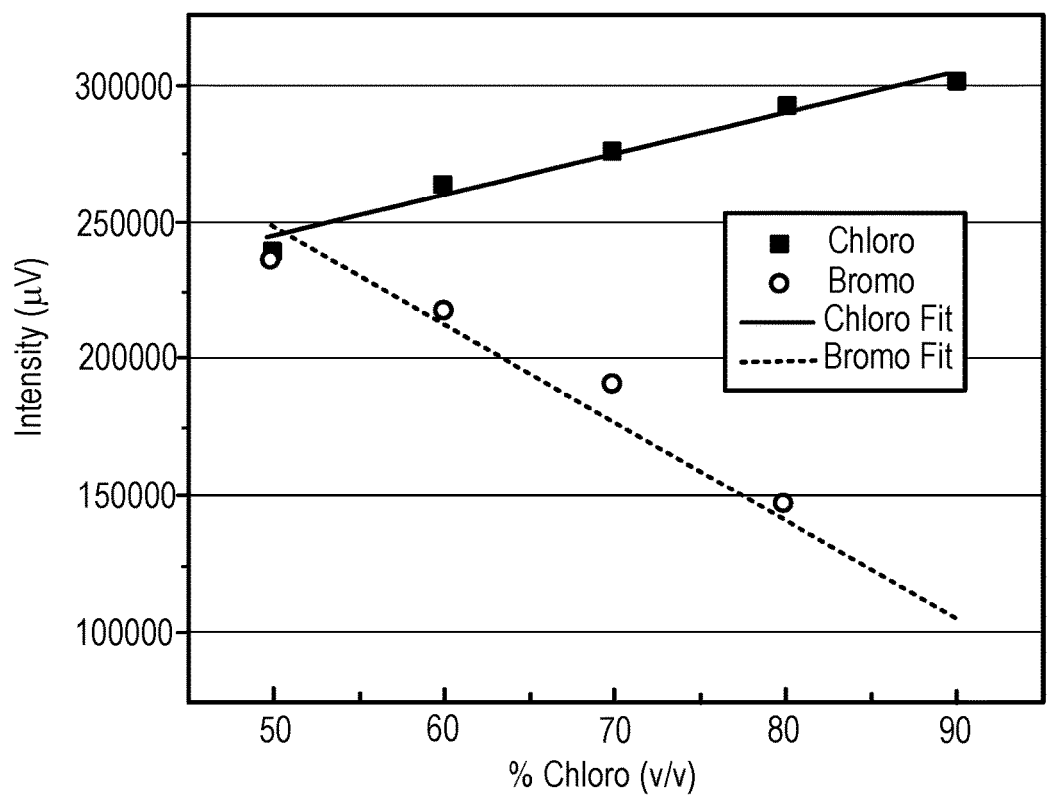

FIGS. 13 and 14 show peak intensity analysis of volumetric mixtures of 4-chlorostyrene and 4-bromostyrene. The results demonstrate a linear response of peak intensity to changing proportions of 4-chlorostyrene nanoparticles. Minor deviations from linear behavior can be explained by the unequal density of monomer units in nanoparticles of different type. The suitable detection resolution allows for these proportional monomer mixtures (whether volumetric or copolymeric) to function as additional distinct tags.

The SDS background is pervasive in all Py-GC/FID measurements on the nanoparticles, which could complicate tag detection in the future if a certain tag is retained as long as the SDS fragments, so its volatilization was studied by exposing a sample of SDS to a set of temperature stages in the pyrolyzer. The temperature of maximum SDS loss would then be used as the drying temperature for all future pyrolysis runs to ensure the removal of all non-polymeric material before analysis.

Figure 15:
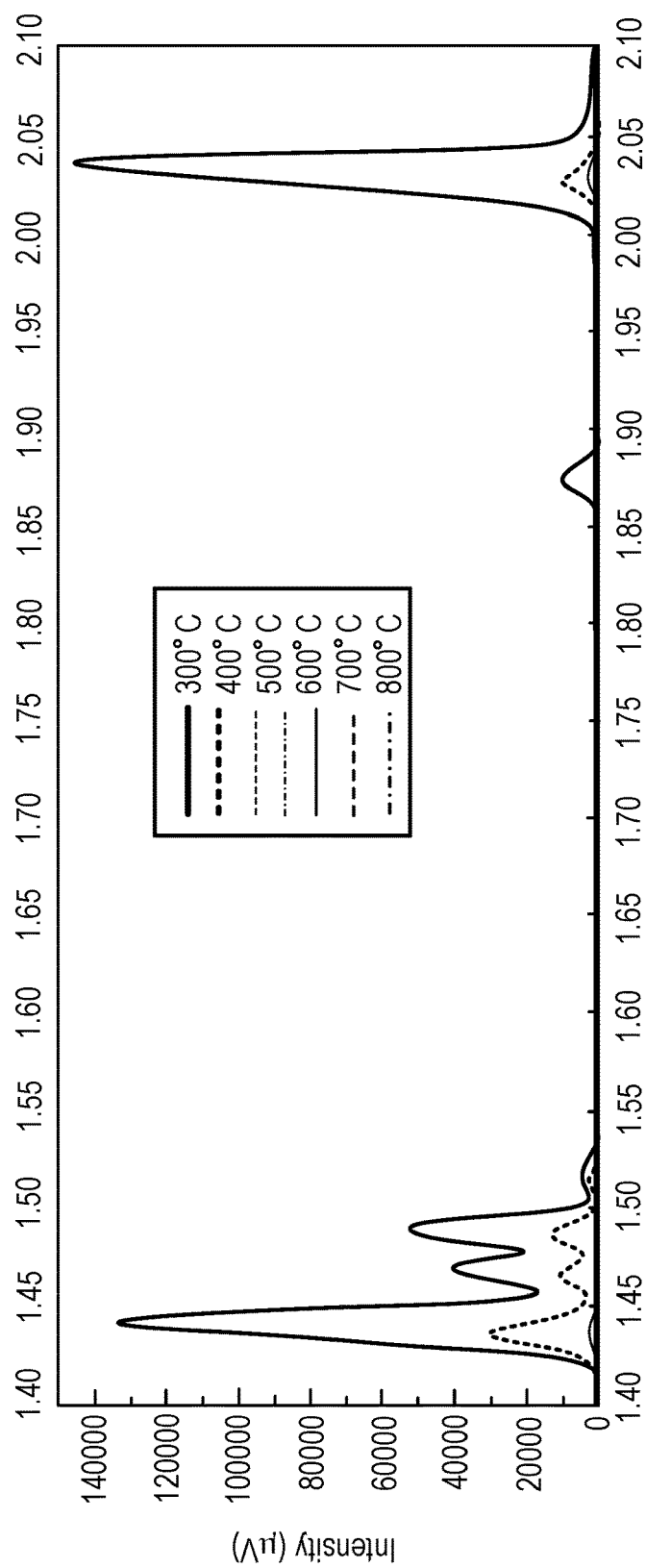
FIG. 15 shows pyrolysis temperature stages on a single sample of surfactant.

The pyrograms at all temperature stages are overlaid in FIG. 15, which shows pyrolysis temperature stages on a single sample of SDS. Each curve represents the amount of material volatilizing at its associated temperature after having been subjected to the previous temperature stage for 30 sec. Between 300° C. and 400° C., the peak intensities dropped by more than a factor of four to near-negligible levels. At 500° C., the SDS signal is almost completely eliminated; however, 500° C. is too close to the degradation temperature of most types of polystyrene, so setting it as the drying temperature could compromise monomer signals and harm limits of detection. Hence, 400° C. was chosen as the appropriate drying temperature and was used for all subsequent pyrolysis runs.

To simulate reservoir conditions, nanoparticle detection was to be attempted in the presence of seawater and crude petroleum. First, aliquots of the p-methylstyrene and the 2,4-dimethylstyrene nanoparticle solutions were separately coated with polyethyleneimine (PEI) to colloidally stabilize them in seawater. The coating process compounded with the introduction to seawater would dilute the particle concentrations to approximately 250-350 ppm, so a large decrease in peak intensity is to be expected. First, a sample of PEI in seawater (SW) was separately pyrolyzed to determine the background signal. Then PEI-coated p-methylstyrene nanoparticles in seawater were pyrolyzed, followed by the pyrolysis of the same solution but with 100 μL of crude Hawiyah petroleum (Oil) mixed in, further followed by the pyrolysis of the same solution with additional PEI-coated 2,4-dimethylstyrene nanoparticles. The results are summarized in FIGS. 16A and 16B, which shows pyrograms of PEI-coated nanoparticles in seawater with and without crude petroleum.

Figure 16:
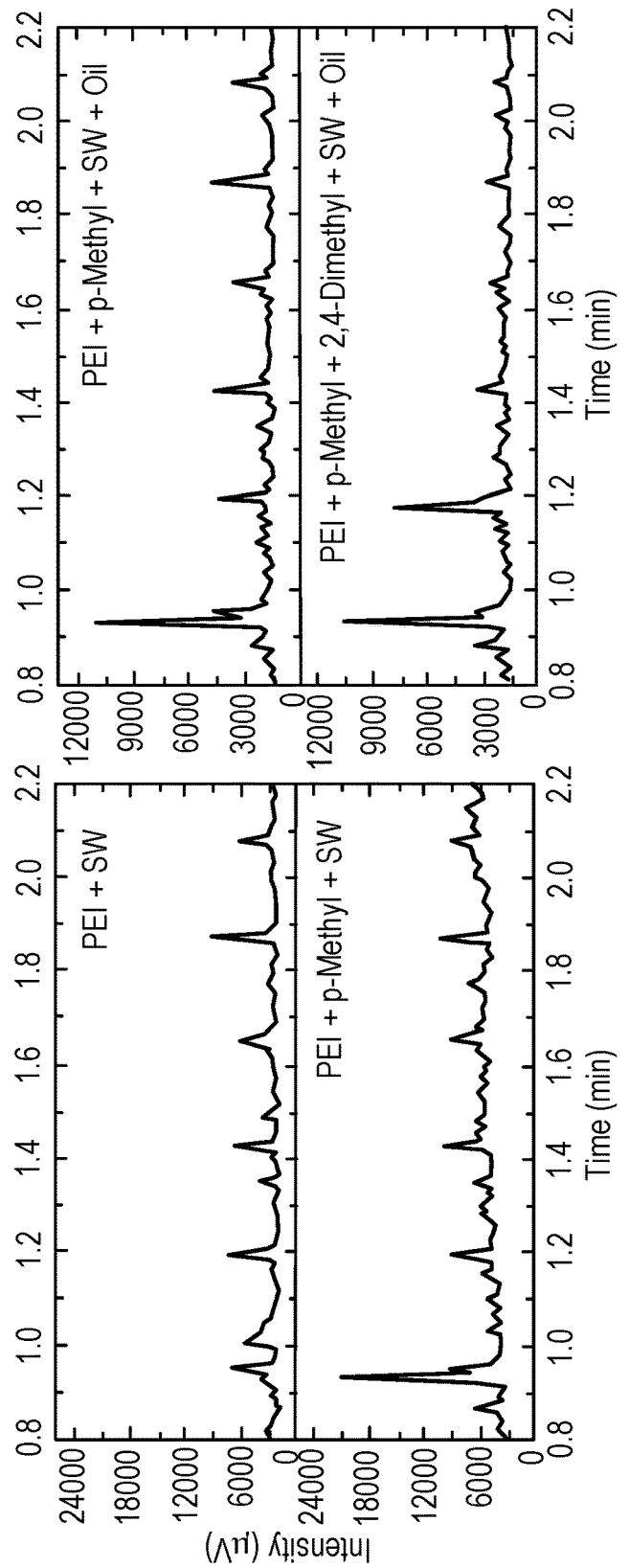
FIGS. 16A and 16B show pyrograms of polymer coated nanoparticles in seawater with and without crude petroleum, respectively.

The top panel in FIG. 16A shows the background signal (PEI+SW). The bottom panel in FIG. 16A (PEI+p-Methyl+SW) demonstrates the detection of p-methylstyrene tags in seawater and in the presence of PEI as shown by the peak at 0.95 min. The top panel in FIG. 16B (PEI+p-Methyl+SW+Oil) demonstrates the detection of the same tag despite the presence of crude petroleum, and the bottom panel in FIG. 16B (PEI+p-Methyl+2,4-Dimethyl+SW+Oil) demonstrates the detection of multiple tags as shown by the additional peak at 1.2 min attributed to 2,4-dimethylstyrene. This shows that tag signal would be hardly affected, if at all, by reservoir conditions when the sample is dried at 400° C. to remove unwanted hydrocarbons before pyrolysis.

Figure 17:
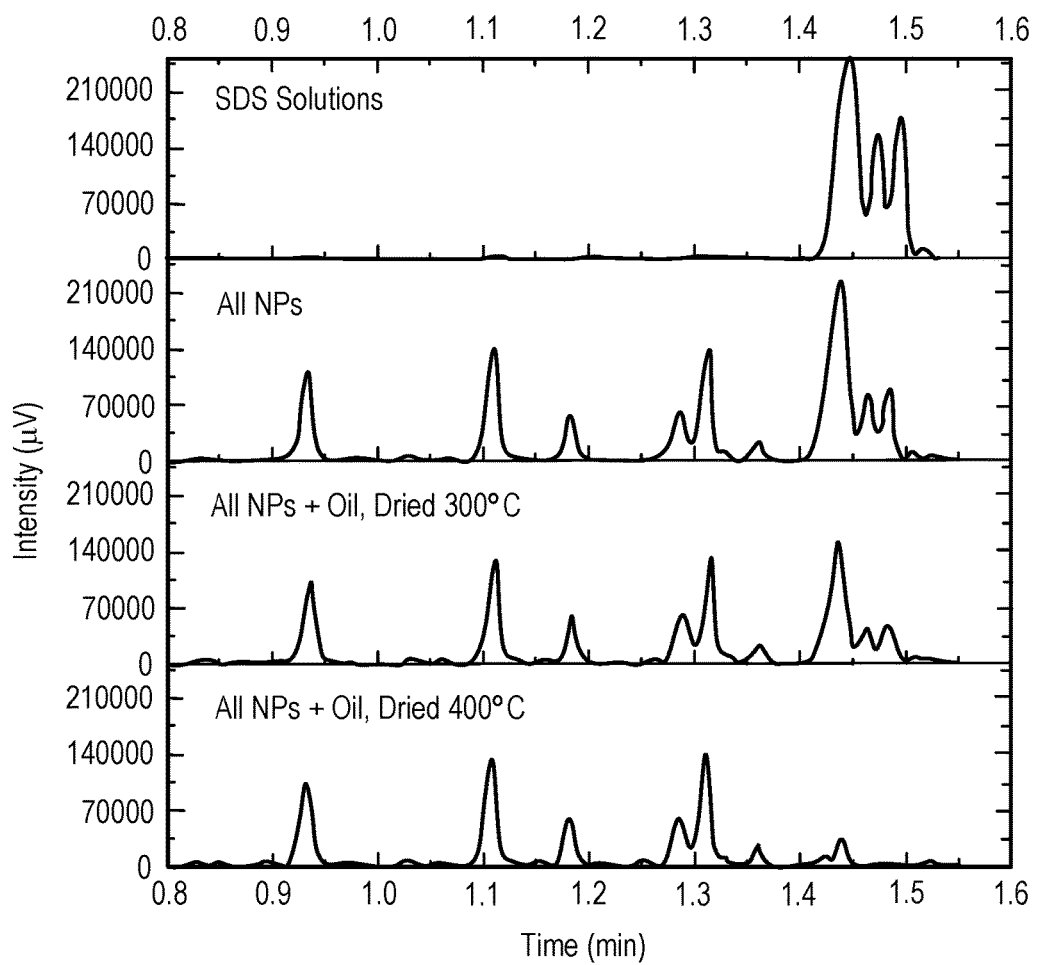
FIG. 17 shows pyrograms of surfactant, polymeric tracers, and polymeric tracers with crude petroleum.

To further test the temporal resolution of Py-GC detection, a volumetric mixture of all six nanoparticle solutions was prepared and pyrolyzed (with drying at 300° C.), and the resulting pyrogram was compared to those of the individual nanoparticles. Afterward, 100 μL of crude petroleum was introduced to the mixture, which was pyrolyzed two separate times: once dried at 300° C., and once dried at 400° C., to observe the effects on the SDS signal. FIG. 17 shows, from top to bottom, pyrograms of: SDS, a volumetric mixture of all 6 nanoparticle solutions dried at 300° C., nanoparticle mixture with 100 μL of Hawiyah crude petroleum dried at 300° C., and nanoparticle mixture with 100 μL of Hawiyah crude petroleum dried at 400° C.

Figure 18:
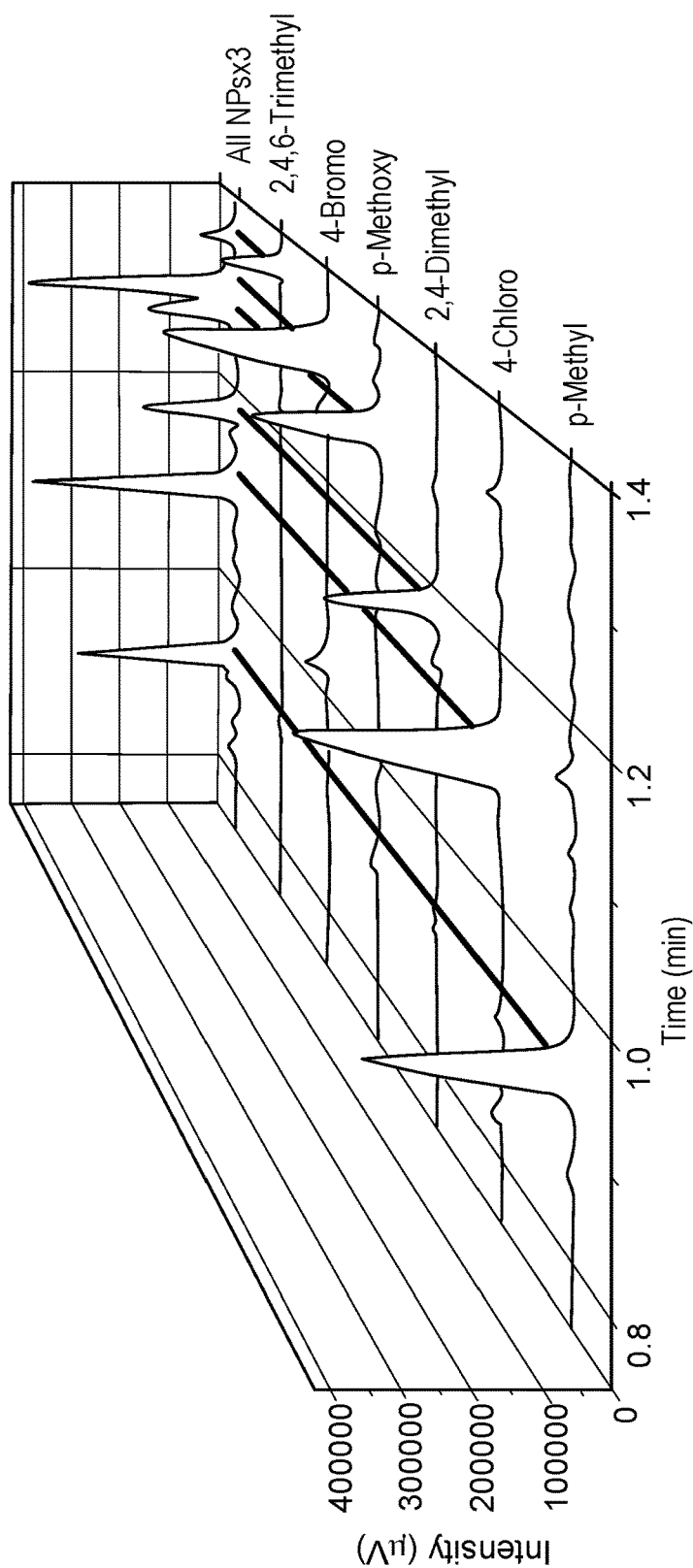
FIG. 18 shows pyrograms of polymeric tracers, each with a distinct monomer.

Not counting the SDS triplet peak, the second panel from the top in FIG. 17 (All NPs) demonstrates 6 distinguishable peaks, each at a retention time corresponding to an individual monomer signal. FIG. 18 cross-references these peaks with constituent signals. The second panel from the bottom in FIG. 17 demonstrates the effects, or lack thereof, of adding crude petroleum to the mixture. The bottom panel in FIG. 17 demonstrates a significant reduction of the SDS triplet peak, effectively clearing the sample space for additional tags if needed.

Example 2

Two additional crosslinked polymer nanoparticle systems were synthesized using monomers of varying masses—namely, styrene and t-butylstyrene. The resulting nanoparticles were dispersed in either deionized water or synthetic seawater to demonstrate that pyrolysis GCMS can be used to detect the polymeric particles in aqueous matrices. The pyrolyzer was programmed to heat the sample to 200° C. for two minutes in order to rid the sample of water followed by heating to 700° C. to decompose the polymeric particle into monomers. The monomers were then analyzed via GCMS to determine their molecular weight.

Styrenic monomers (styrene 99% stabilized (Acros Organics) and 4-tert-butylstyrene 90% stabilized (TCI America)) were purified prior to use by passing the monomer liquid through a short column of basic aluminum oxide for removal of polymerization inhibitor. The polymeric particles were synthesized via a monomer starved approach. In this method, a 100 mL three necked flask equipped with a magnetic stir bar was charged with 50 mL of a 3 wt % solution of IGEPAL CA-897 (Solvay) in deionized water (Milli-Q System, Millipore, USA, 18.2 Me). The vessel was sealed and degassed for 30 minutes by bubbling $N_2$ through the solution. After degassing, 40 mg of 2,2'-azobis(2-methylpropionamidine) dihydrochloride 98% (Acros Organics) was added to the solution under an $N_2$ purge. The pH was adjusted to ~9 using 1M NaOH (aq). The solution was then heated to 80° C. using an oil bath. During the heating stage, a 10 mL syringe was loaded with approximately 3 mL of a 10:1 mixture by volume of the purified styrenic monomer: purified p-divinyl-benzene 85% (Sigma-Aldrich), and loaded onto a Harvard Apparatus PHD 2000 syringe pump. After the solution had been at 80° C. for approximately 10 min (solution temperature verified through use of a thermocouple) the styrenic monomer was added to the solution at a rate of 0.02 mL/min until 2 mL of monomer had been added. The solution was stirred at 80° C. for approximately two hours after the monomer had been added. The solution was then cooled to room temperature and analyzed via dynamic light scattering (DLS) for size and thermal gravimetric analysis (TGA) for solids content.

Figure 19:
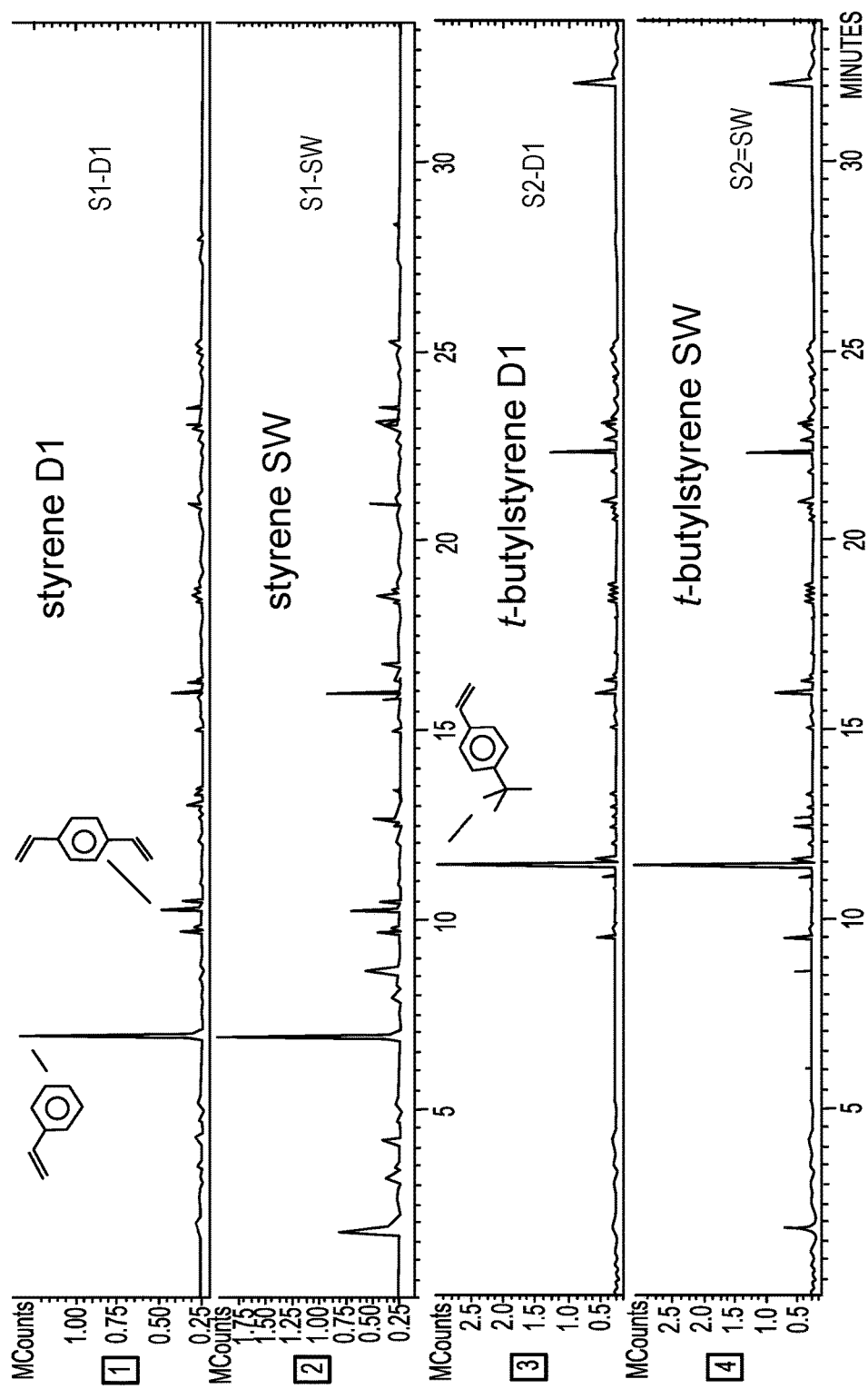
FIG. 19 shows total ion chromatograms (TICs) after pyrolysis of polymeric tracers in aqueous matrices.

The instrument used for pyrolysis-GCMS experiments was a CDS 5250 pyroprobe mounted to a GCMS outfitted with a 30M 35% phenyl column and using electron ionization. 1 μL of sample was used per run.
Pyrolysis Parameters:
Drying stage—200° C. for 2 min
Pyrolysis stage—700° C. for 1 min
Transfer line temperature—300° C.
GCMS Parameters:
Carrier A control—Pflow-He
Split ratio—50:1
Front injector setpoint—300° C.
Oven Program
Initial Temp—40° C.
Initial Hold—2.0 min
Ramp program—12.0° C./min to 300° C. hold for 10.0 min
MSD Parameters:
Type—MS scan
Ion mode—EI+
Start mass—35.00
End mass—550.00
Scan time—0.2 sec FIG. 19 shows total ion chromatograms (TICs) after programmed pyrolysis of polymeric tracers in aqueous matrices: from top to bottom, the panels show polystyrene nanoparticles in deionized water, polystyrene nanoparticles in synthetic seawater, poly-t-butylstyrene nanoparticles in deionized water, and poly-t-butylstyrene nanoparticles in synthetic seawater. The spectra containing styrene and t-butylstyrene are distinct, demonstrating the barcoding capability of the polymeric tracers.

The results in FIG. 19 demonstrate the following characteristics of this approach: (1) polymeric tracers can be cleanly decomposed into their constituent monomers at elevated temperatures and the resulting monomers can be detected via GCMS; (2) programmable pyrolysis permits direct detection of polymeric tracers in complex matrices such as synthetic seawater which would otherwise be unsuitable for GCMS; (3) styrene and t-butylstyrene are easily differentiable by mass, thereby providing evidence of a rich barcoding scheme; and (4) no extraction or isolation steps were performed on the particles, thereby eliminating any time consuming laboratory intervention.

Figure 20:
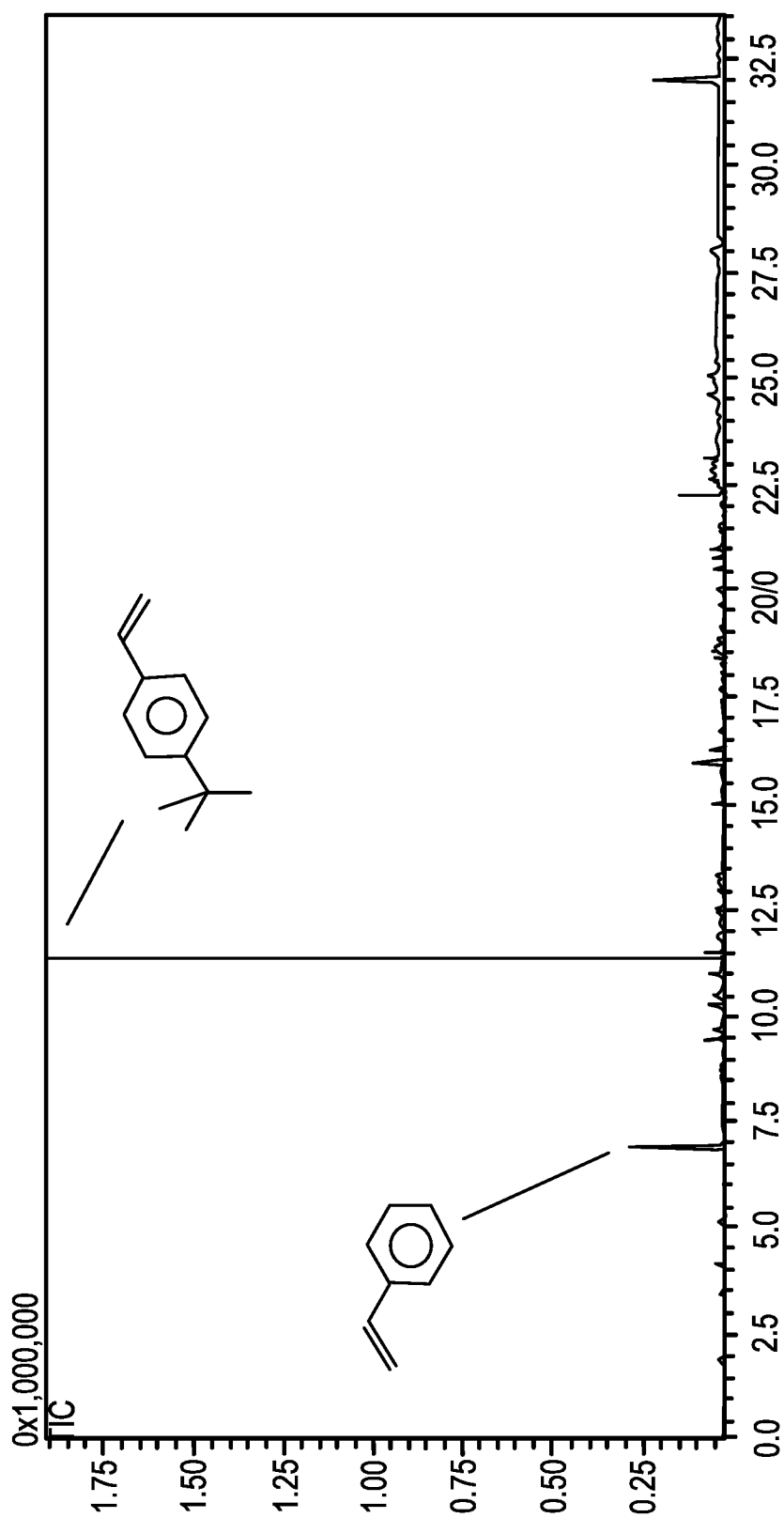
FIG. 20 shows a total ion chromatogram (TIC) after pyrolysis of a mixture of styrene and 4-tert-butylstyrene nanoparticles.

To emphasize the barcoding capability of the approach, a mixture of both polymer particle platforms was prepared in the same synthetic seawater base fluid—not unlike what may occur in the field if two injectors are communicating with one producer. The heterogeneous sample was pyrolyzed and analyzed as in the previous example. The results are shown in FIG. 20. FIG. 20 shows a total ion chromatogram after programmed co-pyrolysis of a mixture of styrene and 4-tert-butylstyrene nanoparticles. Note that ions originating from both monomers show up in the chromatograms, thereby demonstrating the capability to uniquely identify various polymeric materials via pyrolysis-GCMS.

In summary, a polymeric tracer system, composed of various polymeric cores, that is capable of cleanly decomposing into its constituent monomers at specific temperatures has been developed. This approach allows the creation of a library of tracer particles that can be unambiguously detected and identified in highly heterogeneous media such as produced water from oil fields. The synthesis and pyrolysis behaviors of eight unique particle systems as well as mixed particles that contain more than one monomer have been demonstrated. Unambiguous detection of these particles in oily saline water has also been demonstrated.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described as acting in certain combinations and even initially claimed as such, one or more features from a claimed combination can in some cases be excised from the combination, and the claimed combination may be directed to a subcombination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations should not be understood as requiring such separation in all implementations, and it should be understood that the described program components and systems can generally be integrated together in a single software product or packaged into multiple software products.

Further modifications and alternative implementations of various aspects will be apparent to those skilled in the art in view of this description. Accordingly, this description is to be construed as illustrative only. It is to be understood that the forms shown and described are to be taken as examples of implementations. Elements and materials may be substituted for those illustrated and described, parts and processes may be reversed, and certain features may be utilized independently, all as would be apparent to one skilled in the art after having the benefit of this description. Accordingly, the description of example implementations does not define or constrain this disclosure. Other changes, substitutions, and alterations are also possible without departing from the spirit and scope of this disclosure.

What is claimed is:

1. A method of tracing fluid flow in a subterranean formation, comprising:
    providing a polymeric tracer comprising a polymeric nanoparticle to an injector location in the subterranean formation to flow through the subterranean formation from the injector location to a producer location in the subterranean location, wherein the polymeric nanoparticle comprises a polymeric core, a polymeric layer surrounding the polymeric core, and a surfactant layer between the polymeric core and the polymeric layer;
    collecting an aqueous sample from the producer location;
    removing water from the aqueous sample to yield a dehydrated sample;
    pyrolyzing the dehydrated sample to yield a gaseous sample; and
    detecting a pyrolization product of the polymeric core in the gaseous sample, wherein presence of the pyrolization product in the gaseous sample is indicative of presence of the polymeric tracer in the aqueous sample.

2. The method of claim 1, comprising protecting the polymeric core in reservoir conditions of the subterranean formation via the polymeric layer, wherein the polymeric layer is a protective coating, and wherein the pyrolization product comprises a constituent monomer of a polymer of the polymeric core or a monomer substituent on the constituent monomer, or a combination thereof.

3. The method of claim 1, wherein the polymeric core comprises polystyrene, polyacrylate, or polymethacrylate, and wherein the polymer layer comprises polyethyleneimine (PEI) or a crosslinked carbohydrate-based coating.

\* \* \* \* \*